(12) United States Patent
Fields et al.

(10) Patent No.: US 12,315,357 B2
(45) Date of Patent: May 27, 2025

(54) SYSTEMS AND METHODS FOR DETECTING WATER DAMAGE USING ENERGY-HARVESTING SENSORS

(71) Applicant: STATE FARM MUTUAL AUTOMOBILE INSURANCE COMPANY, Bloomington, IL (US)

(72) Inventors: Brian Mark Fields, Phoenix, AZ (US);
Shawn M. Call, Bloomington, IL (US);
Jaime Skaggs, Chenoa, IL (US);
Matthew S. Megyese, Bloomington, IL (US)

(73) Assignee: STATE FARM MUTUAL AUTOMOBILE INSURANCE COMPANY, Bloomington, IL (US)

( * ) Notice: Subject to any disclaimer, the term of this patent is extended or adjusted under 35 U.S.C. 154(b) by 44 days.

(21) Appl. No.: 18/200,281

(22) Filed: May 22, 2023

(65) Prior Publication Data
US 2024/0144807 A1 May 2, 2024

Related U.S. Application Data

(60) Provisional application No. 63/434,291, filed on Dec. 21, 2022, provisional application No. 63/427,146, (Continued)

(51) Int. Cl.
G08B 21/20 (2006.01)
E03B 7/07 (2006.01)
(Continued)

(52) U.S. Cl.
CPC ............. *G08B 21/20* (2013.01); *E03B 7/072* (2013.01); *G01D 21/02* (2013.01); *G01M 3/045* (2013.01);
(Continued)

(58) Field of Classification Search
USPC ........ 340/604, 539.1, 488, 507, 525, 538.11, 340/539.22, 539.12, 602, 592, 612,
(Continued)

(56) References Cited

U.S. PATENT DOCUMENTS

2007/0208841 A1* 9/2007 Barone ............... B61L 15/0027
709/223
2011/0285527 A1* 11/2011 Arms .................... G07C 5/085
340/539.1

(Continued)

*Primary Examiner* — Daniel Previl
(74) *Attorney, Agent, or Firm* — MARSHALL, GERSTEIN & BORUN LLP

(57) ABSTRACT

A system for detecting water damage to a structure may include a plurality of energy-harvesting sensors on or within the structure, each sensor being configured to (i) generate sensor data indicative of one or more characteristics of air, construction materials, and/or water within the structure and (ii) generate power for operating the sensor responsively to an external stimulus other than an electrical power source. One or more processors of the system receive sensor data generated by the energy-harvesting sensors, detecting water damage to the structure by analyzing at least the sensor data, and cause an indication of the detected water damage to be presented to a user.

20 Claims, 12 Drawing Sheets

Related U.S. Application Data filed on Nov. 22, 2022, provisional application No. 63/423,362, filed on Nov. 7, 2022, provisional application No. 63/421,466, filed on Nov. 1, 2022.

(51) Int. Cl.
| | |
|---|---|
| *G01D 21/02* | (2006.01) |
| *G01M 3/04* | (2006.01) |
| *G01M 5/00* | (2006.01) |
| *G06F 30/27* | (2020.01) |
| *G06N 3/088* | (2023.01) |
| *H02J 50/00* | (2016.01) |
| *E03B 7/00* | (2006.01) |
| *G06F 113/08* | (2020.01) |

(52) U.S. Cl.
CPC ........... *G01M 5/0033* (2013.01); *G06F 30/27* (2020.01); *G06N 3/088* (2013.01); *H02J 50/001* (2020.01); *E03B 7/003* (2013.01); *G06F 2113/08* (2020.01)

(58) Field of Classification Search
USPC .................................................. 340/636.18
See application file for complete search history.

(56) References Cited

U.S. PATENT DOCUMENTS

| | | | |
|---|---|---|---|
| 2017/0258585 A1* | 9/2017 | Marquez | A61B 5/4851 |
| 2019/0013960 A1* | 1/2019 | Sadwick | G08C 17/02 |
| 2019/0324444 A1* | 10/2019 | Cella | G06N 3/088 |

* cited by examiner

SYSTEMS AND METHODS FOR DETECTING WATER DAMAGE USING ENERGY-HARVESTING SENSORS

CROSS-REFERENCE TO RELATED APPLICATIONS

This application claims the benefit of U.S. Provisional Patent Application Nos. 63/421,466 (filed on Nov. 1, 2022), 63/423,362 (filed on Nov. 7, 2022), 63/427,146 (filed on Nov. 22, 2022), and 63/434,291 (filed on Dec. 21, 2022). The entire disclosure of each of the above-identified applications is hereby incorporated herein by reference.

TECHNICAL FIELD

The present application relates generally to systems, methods, and techniques for detecting water damage.

BACKGROUND

Water is a leading cause of costly damage to homes and other structures, whether leaking from a pipe or fixture, from an appliance, through a roof, or through a foundation. At the same time, such damage may be notoriously difficult to detect and/or prevent. While various devices are currently available for detecting water-related problems (e.g., battery-powered or plug-in water/flood detector devices, or leak detectors that may be affixed to water heaters, etc.), such devices may tend to be narrowly tailored to detecting specific types of water issues in specific locations (i.e., in the near vicinity of the device), and/or may be unable to protect the entire home. Moreover, such devices may be generally incapable of identifying more complex water-related issues, and in many cases may merely serve to provide notice after water damage has already occurred.

Moreover, many home owners may be unaware of how specific factors (e.g., specific fixtures, specific appliances, irrigation systems, specific family members, etc.) contribute to the overall water usage indicated on their monthly water bills, and therefore may be unable to take effective, targeted measures with respect to reducing water usage. Conventional techniques may have additional inefficiencies, encumbrances, ineffectiveness, and other drawbacks.

SUMMARY

In general, the present embodiments may relate to, inter alia, computer-implemented methods, devices, and/or systems that more effectively and thoroughly protect homes or other structures from water damage. The present embodiments may additionally or alternatively provide computer-implemented methods, devices, and/or systems that facilitate more efficient usage of water (e.g., to lower water bills, and/or for more environmentally-responsible water usage).

More specifically, in one aspect of this disclosure, various sensors (e.g., air quality sensors, water sensors, thermal imaging sensors, cameras, impedance or pressure sensors, audio detectors or recorders, etc.), which may be part of a mesh network architecture, are used to detect or infer that water damage has occurred or likely will occur within a home or other structure. Indicia of water damage may include, for example, differentials (or other anomalies) in humidity or temperature, and/or airborne particle counts (e.g., mold, spore, and/or fungus). Other factors may also affect the determination/prediction, such as the amount of time water is pooled or actively entering the home, the presence of structural water outlets (e.g., drains) or inlets near detected water, the absorption rate of walls and/or floors in the area of standing/pooled water, and/or the amount of air movement near a location of standing/pooled or a water intrusion. The sensors may be embedded in construction materials and/or appliances, manually installed, affixed to the home, or temporarily brought into a home for an inspection. Warnings may be generated based upon anomalies from a baseline model, and/or using machine learning.

In one aspect, a computer system for detecting water damage to a structure may be provided. The method may include: (1) a plurality of energy-harvesting sensors on or within the structure, wherein each sensor of the plurality of energy-harvesting sensors may be configured to (i) generate sensor data indicative of one or more characteristics of air, construction materials, and/or water within the structure, and/or (ii) generate power for operating the sensor responsively to an external stimulus other than an electrical power source; (2) one or more processors; and/or (3) one or more memories storing instructions. The instructions, when executed by the one or more processors, cause the one or more processors to perform a method comprising: (1) receiving sensor data generated by the plurality of energy-harvesting sensors; (2) detecting water damage to the structure by analyzing at least the sensor data; and/or (3) causing an indication of the detected water damage to be presented to a user. The system may include additional, less, or alternate functionality, including that discussed elsewhere herein.

In another aspect, a computer-implemented method for detecting water damage to a structure may be provided. The method may include: (1) receiving sensor data generated by a plurality of energy-harvesting sensors on or within the structure, wherein each sensor of the plurality of energy-harvesting sensors may be configured to (i) generate sensor data indicative of one or more characteristics of air, construction materials, and/or water within the structure, and/or (ii) generate power for operating the sensor responsively to an external stimulus other than an electrical power source; (2) detecting, by one or more processors, water damage to the structure by analyzing at least the sensor data; and/or (3) causing, by the one or more processors, an indication of the detected water damage to be presented to a user. The method may include additional, less, or alternate actions, including those discussed elsewhere herein.

In another aspects, one or more tangible, non-transitory, computer-readable media store instructions that, when executed by one or more processors, cause the one or more processors to: (1) receive sensor data generated by a plurality of energy-harvesting sensors on or within the structure, wherein each sensor of the plurality of energy-harvesting sensors is configured to (i) generate sensor data indicative of one or more characteristics of air, construction materials, and/or water within the structure, and/or (ii) generate power for operating the sensor responsively to an external stimulus other than an electrical power source; (2) detect water damage to the structure by analyzing at least the sensor data; and/or (3) cause an indication of the detected water damage to be presented to a user. The instructions may direct additional, less, or alternate functionality, including that discussed elsewhere herein.

Advantages will become more apparent to those skilled in the art from the following description of the preferred embodiments which have been shown and described by way of illustration. As will be realized, the present embodiments may be capable of other and different embodiments, and their details are capable of modification in various respects.

Accordingly, the drawings and description are to be regarded as illustrative in nature and not as restrictive.

BRIEF DESCRIPTION OF THE DRAWINGS

The Figures described below depict various aspects of the systems and methods disclosed therein. It should be understood that each Figure depicts an embodiment of a particular aspect of the disclosed systems and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and are instrumentalities shown, wherein.

The Figures depict preferred embodiments for purposes of illustration only. One skilled in the art will readily recognize from the following discussion that alternative embodiments of the systems and methods illustrated herein may be employed without departing from the principles of the invention described herein.

DETAILED DESCRIPTION

The embodiments described herein relate to, inter alia, systems, methods, and techniques for detecting and/or predicting water damage and/or water intrusion, and/or for monitoring water usage, in a home or other structure.

Exemplary Computer System

Figure 1:
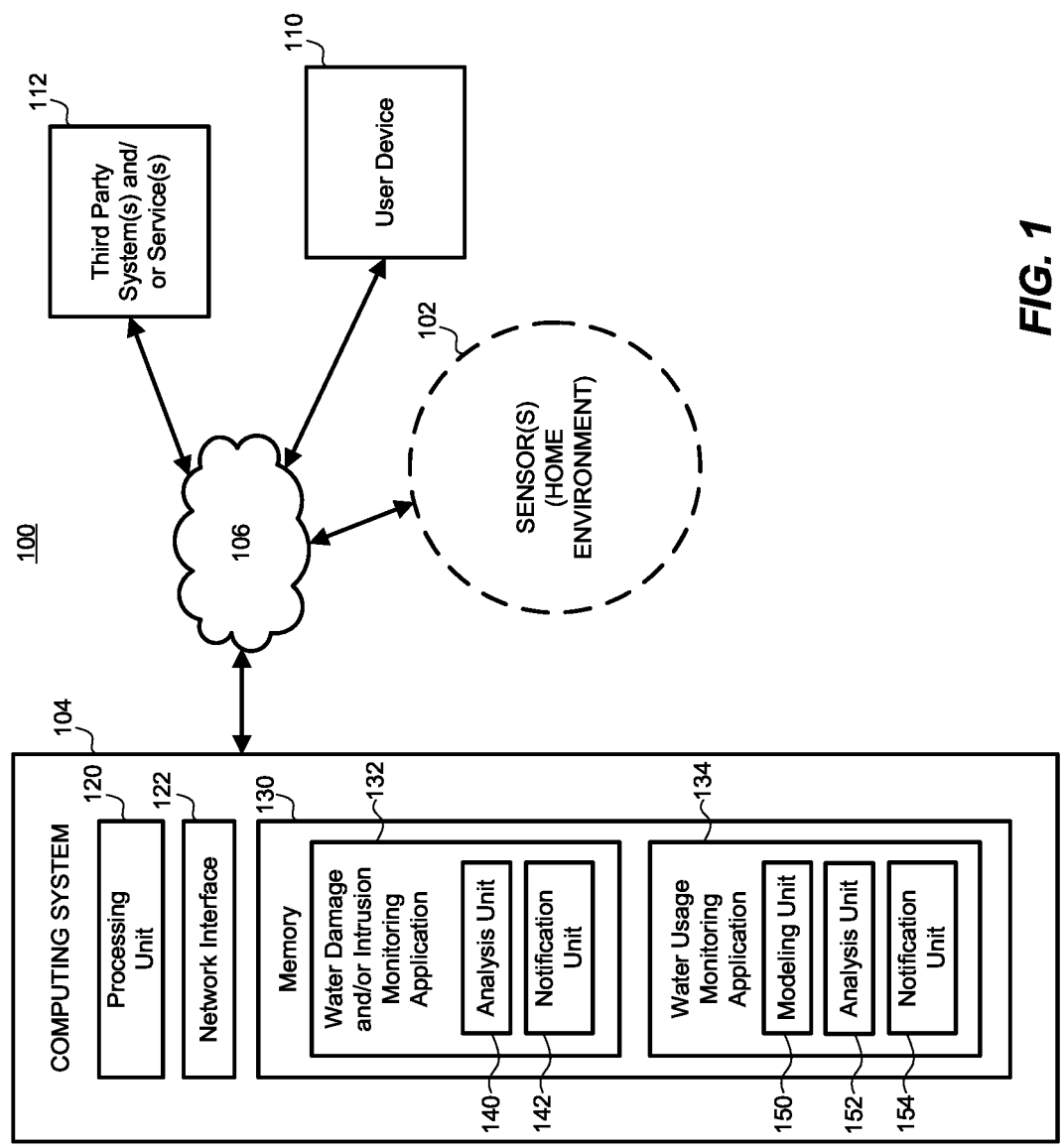
FIG. 1 is a block diagram of an exemplary computer system for detecting and/or predicting water damage and/or intrusion, and/or monitoring water usage, in a home or other structure, according to one embodiment.

FIG. 1 is a simplified block diagram of an exemplary computer system 100 in which one or more techniques of the present disclosure may be implemented. The exemplary system 100 includes one or more sensors 102 in a home environment, a computing system 104 communicatively coupled to the sensor(s) 102 via a network 106, a user device 110 communicatively coupled to the computing system 104 via the network 106, and one or more third party systems and/or services 112 (also referred to herein as "third parties 112") coupled to the computing system 104 via the network 106.

It is understood that a "home" or "home environment" as referred to herein may instead, in other embodiments, be any other type of structure in which water is used for one or more purposes. For example, the structure may be a single-family home, an apartment unit or building, an office building, a manufacturing facility, a storage building, and so on. Moreover, unless the context of usage clearly indicates a more specific meaning, references to a thing or event (e.g., a sensor, fixture, or other entity, or water damage, or a leak, etc.) being or taking place "within" a home or structure may mean that the thing or event so described is within (or takes place within) an internal space of the home or structure (e.g., standing water in a basement or inside an internal wall, or wet drywall, etc.), and/or is on and/or within (or takes place on and/or within) an exterior portion of the home or structure (e.g., siding materials or window frames with water damage, etc.).

The network 106 may be a single communication network, or may include multiple communication networks of one or more types (e.g., one or more wired and/or wireless personal or local area networks (PANs or LANs), and/or one or more wide area networks (WANs) such as the Internet). In some embodiments, the network 106 includes multiple, entirely distinct networks (e.g., one or more networks for communications between computing system 104 and user device 110, and a separate, Bluetooth or wireless LAN (WLAN) network for communications between computing system 104 and sensor(s) 102, and so on).

The home environment in which the sensor(s) 102 are located may include the home itself, and/or an area around the home (e.g., soil sensors in a yard of the home). The sensor(s) 102 may include any sensor(s) capable of measuring or detecting (alone, or with subsequent processing such as image processing) physical characteristics that are directly or indirectly indicative of the current, past, and/or future presence of water, water damage, water intrusion, and/or water usage. To this end, the sensor(s) 102 may measure/detect any characteristic(s) of air, construction materials, and/or water within and/or outside the home, such as air temperature, air humidity, air movement, air quality (e.g., airborne particle counts such as for mold, spores, and/or fungus), pressure sensors, moisture of construction materials (e.g., drywall, beams, studs, foundation wall elements, etc.), impedance of construction materials, the presence of standing/pooled water, the flow of water, water capacity of soil, conductivity of soil, saturation of soil, the presence of snow, rain, or standing water (e.g., based upon camera or thermal images and image processing), and so on.

In some embodiments, the sensor(s) 102 include home-mounted sensors (e.g., sensors that may be affixed to or within a wall, or to an appliance, etc.) and/or outdoor sensors (e.g., soil or irrigation system sensors). Additionally or alternatively, the sensor(s) 102 may include sensors embedded in construction materials of the home. For example, during a manufacturing process, beams, drywall sheets, floor boards, and/or other construction materials may include embedded sensors that are wired or wireless. Sensor(s) 102 may include sensors powered by batteries, sensors powered by plugging into an electrical outlet of the home, and/or energy-harvesting sensors that are configured to generate power for operating the sensor responsively to an external stimulus, without requiring an external electrical power source (e.g., without requiring an electrical outlet or power generator).

Energy-harvesting sensors may be configured to generate operational power (i.e., power for operating the sensor, including any communications provided by the sensor) responsively to, for example, water flowing past the sensor or a temperature differential across two regions (e.g., nodes) of the sensor. Other examples include sensors that include a sponge-like material that expands when wet, with the sensor generating operational power responsively to the material expanding, and/or sensors that include one or more solar cells, with the sensor generating operational power responsively to the solar cell(s) collecting solar energy. Energy-harvesting sensors may be particularly advantageous in hard-to-access areas, such as inside walls or crawlspaces of a home, and/or in embodiments where at least some of the sensor(s) 102 are embedded within construction materials.

Energy-harvesting sensors may be installed within the home and/or outside the home in locations that are most appropriate for the energy-harvesting technique. For example, sensors powered by water flow may be positioned/installed within pipes or fixtures of the structure, and solar-powered sensors may be positioned/installed in sunlit areas (e.g., near windows, or within exterior walls but with solar cells protruding outside the home). As another example, sensors powered by temperature differentials may be positioned/installed proximate to a water heater within the home, where leaking water (and/or the air near leaking water) would likely have a higher temperature than the ambient room temperature. As with battery-powered and electricity-powered sensors, energy-harvesting sensors may detect/measure/sense any suitable characteristic(s) of air, construction materials, and/or water.

In some embodiments, the energy-harvesting sensors include one or more wireless radio frequency (RF) based energy-harvesting sensors. For example, the wireless RF based energy-harvesting sensor(s) may gather and store small amounts of energy from wireless RF signals in the home environment, such as WiFi and/or other RF signals. The wireless RF signals may be generated or triggered by the application 132 or application 134 of computing system 104 on a periodic basis, for example. In some embodiments, the sensor(s) can use this stored energy to power a notification of a sensed characteristic of air, construction materials, and/or water. For example, the sensor(s) may use the harvested energy to power a transmitter that sends an indication of a sensed characteristic to the computing system 104, for processing by application 132 or application 134. Even if the sensor(s) is/are only capable of harvesting a small amount of energy, this may satisfy the low power requirements of relatively infrequent and/or short-range transmissions/notifications.

The user device 110 may be any suitable mobile computing device with communication, user input, and display capabilities, such as a smartphone, a smart watch, smart glasses, or a virtual or augmented reality headset device, for example. Alternatively, the user device 110 may be a laptop computer, a desktop computer, or any other suitable computing device. While not shown in FIG. 1, the user device 110 includes one or more processors, and one or more memories (e.g., non-volatile memory) storing instructions that, when executed by the processor(s), cause the processor(s) to perform any of the operations discussed herein with respect to the user device 110.

The computing system 104 may be in or near the home. For example, the computing system 104 may be a dedicated system within the home, or may be a system that also provides other functionality (e.g., a system with home security features). In other examples, the computing system 104 is in whole or in part remote from the home environment and sensor(s) 102. In some embodiments, the functionality of the computing system 104 described herein is instead provided by the user device 110 (e.g., one or more mobile apps installed on the user device 110), and the computing system 104 may be omitted.

The computing system 104 may include any suitable computing device or devices, such as a server, a desktop computer, a laptop computer, or a tablet computer, for example, or a dedicated computing device/system. The computing system 104 includes processing unit 120, a network interface 122, and memory 130. The processing unit 120 includes one or more processors, each of which may be a programmable microprocessor that executes software instructions stored in memory 130 to execute some or all of the functions of the computing system 104 as described herein. The processing unit 120 may include one or more central processing units (CPUs) and/or one or more graphics processing units (GPUs), for example. In some embodiments, however, a subset consisting of one or more of the processors in the processing unit 120 may include processors that do not execute software instructions (e.g., application-specific integrated circuits (ASICs), field-programmable gate arrays (FPGAs), etc.).

The network interface 122 may include any suitable hardware (e.g., front-end transmitter and receiver hardware), firmware, and/or software configured to use one or more communication protocols to communicate with external devices and/or systems (including the sensor(s) 102) via the network 106. For example, the network interface 122 may include an IEEE 802.11 WLAN or Ethernet interface, and/or a Bluetooth interface, etc. In some embodiments, the sensor(s) 102 form a mesh network, with centralized or distributed control.

The memory 130 may include one or more volatile and/or non-volatile memories. Any suitable memory type or types may be included in the memory 130, such as a read-only memory (ROM) and/or a random access memory (RAM), a flash memory, a solid-state drive (SSD), a hard disk drive (HDD), and so on. Collectively, the memory 130 may store the instructions of one or more software applications, the data received/used by those applications, and the data output/generated by those applications.

In the exemplary system 100, the memory 130 stores the software instructions of a water damage and/or intrusion monitoring application 132, also referred to herein as "WDIM application 132," and the software instructions of a water usage monitoring application 134, also referred to herein as "WUM application 134." In some embodiments, however, the memory 130 only stores WDIM application 132, only stores WUM application 134, or stores a single application that provides the functionality of both applications 132, 134. Moreover, in some alternative embodiments, WDIM application 132 only provides the water damage monitoring functionality described herein, or only provides the water intrusion monitoring functionality described herein.

The example WDIM application 132 of FIG. 1 includes an analysis unit 140 and a notification unit 142. Generally, the analysis unit 140 processes data indicative of various factors, such as sensor data generated by sensor(s) 102, locally stored/known information (e.g., information relating to home configuration or layout, appliances in the home, etc.), and/or data from third parties 112 (e.g., weather data, social media data, etc.), in order to detect/identify existing water damage to the home and/or water intrusion into the home, and/or to predict (e.g., detect/identify a risk of) future water damage and/or water intrusion.

The analysis unit 140 may process any of the type(s) of sensor data discussed above to detect or predict water damage and/or water intrusions. To this end, the analysis unit 140 may use any suitable rules or algorithms (e.g., comparing sensor data values to thresholds), and/or one or more machine learning models (e.g., trained neural network(s)). In the latter case, the machine learning model(s) may include one or more models trained (e.g., by computing system 104 or another computing system) using labeled training data, and/or one or more models implementing unsupervised machine learning techniques (e.g., an anomaly detection technique such as clustering). In some embodiments, the analysis unit 140 includes different machine learning models (e.g., different neural networks) for water damage detection/prediction and water intrusion detection/prediction, and/or different machine learning models for different types of water damage (e.g., wet construction materials, standing water, leak, etc.) and/or for different types of water intrusion (e.g., foundation, roof, etc.).

In some embodiments, to more intelligently assess whether water damage has occurred or might occur, the analysis unit 140 jointly analyzes sensor data from of a particular type of sensor among sensor(s) 102, in conjunction with one or more other factors (e.g., conditions represented by other types of sensors among sensor(s) 102, and/or factors associated with non-sensor data). For example, the analysis unit 140 may compare both humidity readings and estimated airborne particle counts to respective thresholds, and determine that water damage exists if both thresholds are exceeded (e.g., with one threshold value depending upon the value of the other). As another example, the analysis unit 140 may jointly analyze sensor data and data indicative of one or more factors associated with an interior of the home (e.g., known characteristics of the home such as presence or absence of water outlets and/or inlets, wall and/or appliance configuration, and/or wall and/or floor absorption rates in a particular area of the home). As more specific examples, the analysis unit 140 may generate an indication of actual or potential water damage when a humidity sensor detects high humidity in an area that is known to be in a small, enclosed space, or may apply a higher threshold for water moisture in a room or area that is known to have an outlet such as a drain. Non-sensor data may be entered or downloaded by a user of user device 110, for example, and/or may be stored in the memory 130.

In some embodiments, the non-sensor data analyzed by analysis unit 140 includes data from third parties 112 and/or user device 110, such as current or predicted weather, climate data, and/or information relating to other homes in the area (e.g., information derived from data collected by other systems similar to computing system 104 in other homes in the neighborhood, and/or derived from social media data representing posts or other inputs from neighbors and relating to water conditions in or around the neighbors' homes, etc.). In one exemplary embodiment, the analysis unit 140 lowers the threshold for humidity in a home by an amount that the analysis unit 140 determines based upon how long the weather has been rainy (and/or based upon how many neighbors have water problems, etc.), and indicates/outputs a high risk of water damage if a sensor in the home indicates that the lowered humidity threshold has been exceeded.

In some embodiments, the analysis unit 140 generates a baseline model for the home based at least in part upon sensor data from a first, earlier time or time range, and then detects or predicts water damage by comparing sensor data from a second, later time or time range to the baseline model (i.e., by detecting sufficiently large anomalies/deviations relative to the baseline model). The baseline model may include a set of parameters (e.g., humidity in particular rooms/areas, average daily water usage per appliance or per room/area, etc.), and "normal" or "expected" ranges of values for each parameter. The analysis unit 140 may detect anomalies by determining when values differ from the normal range by amounts that exceed respective thresholds, for example, or using another suitable technique (e.g., by representing the set of parameters as a multi-dimensional space and determining whether the distance between (1) a first vector representing the current sensor and/or other data/values, and (2) a second vector representing "normal" sensor and/or other data/values, exceeds a threshold amount).

In some embodiments, to more intelligently assess whether water intrusion has occurred or might occur, the analysis unit 140 receives and analyzes data indicative of one or more factors associated with the external environment. For example, the analysis unit 140 may determine that water intrusion has occurred, is occurring, or will occur based upon a known or detected (by sensor(s) 102) water capacity of soil around the home, a known or detected (by sensor(s) 102) conductivity of the soil, and/or a detected (by sensor(s) 102) water saturation of the soil. Other example factors may include data indicative of snow, rain, and/or standing water (e.g., based upon images captured by sensor(s) 102 and image processing of the analysis unit 140), irrigation of land around the home (e.g., data generated by a sensor of the irrigation system or controller data indicative of a programmed irrigation schedule), and/or current or future weather and/or climate (e.g., data provided by one or more third parties 112).

In some embodiments, to better assess whether water intrusion has occurred, is occurring, or will occur, the analysis unit 140 also analyzes data indicative of one or more factors associated with an interior of the home. For example, in addition to one or more factors associated with the exterior environment, the analysis unit 140 may determine that water intrusion has occurred, is occurring, or will occur based upon data indicative of foundation characteristic(s) (e.g., as collected by one or more sensors of sensor(s) 102 that are embedded within the foundation), standing water within the home (e.g., as collected by one or more water sensors of sensor(s) 102), an amount or percentage of time that the foundation is wet and/or water is entering through the foundation, and/or a known configuration and/or contents of the home (e.g., whether the home includes a basement, whether the basement has a sump pump, etc.).

Similar to the embodiments described above in connection with water damage, the analysis unit 140 can, in some embodiments, detect or predict water intrusion by analyzing non-sensor data from third parties 112 and/or user device 110, such as current or predicted weather, climate data, and/or information relating to other homes in the area (e.g., information derived from data collected by other systems similar to computing system 104 in other homes in the neighborhood, and/or derived from social media data representing posts or other inputs from neighbors describing water intrusions in their homes, etc.). In one example embodiment, the analysis unit 140 lowers the threshold for humidity in the basement of a home by an amount that the analysis unit 140 determines based upon how long the weather has been rainy (and/or based upon how many neighbors have reported water intrusions, etc.), and indicates/outputs a high risk of water intrusion if a sensor in the basement indicates that the lowered humidity threshold has been exceeded.

Similar to the embodiments described above in connection with water damage, the analysis unit 140 can, in some embodiments, generate a baseline model for the home and/or exterior (e.g., soil or yard) environment based at least in part upon sensor data from a first, earlier time or time range, and then detects or predicts water intrusion by comparing sensor data from a second, later time or time range to the baseline model (i.e., by detecting sufficiently large anomalies/deviations relative to the baseline model). The baseline model may include a set of parameters (e.g., humidity in particular rooms/areas, foundation moisture, etc.), and "normal" or "expected" ranges of values for each parameter. The analysis unit 140 may detect anomalies by determining when values differ from the normal range by amounts that exceed respective thresholds, for example, or using another suitable technique (e.g., by representing the set of parameters as a multi-dimensional space as described above).

The notification unit 142 generates notifications relating to water damage and/or intrusion, and directly or indirectly transmits the notifications to the user device 110 (e.g., via the network interface 122 and network 106, to be presented on a graphical user interface generated by an application executing on the user device 110, or as a text message or email, etc.) for display to the user. For example, the notification unit 142 may cause the user device 110 to present an indication (e.g., alert) of detected or predicted water damage or water intrusion. The indication may be a statement generally indicating the presence or likelihood of water damage or intrusion, or a percent (e.g., 60%) or degree (e.g., "medium" or "high") likelihood of water damage or intrusion, for example.

In some embodiments, the analysis unit 140 determines a location where in the home the water damage or intrusion is occurring, and indicates the location in the notification. The analysis unit 140 may determine this location based upon the known locations of the sensor(s) 102 and, more specifically, based upon the known location of the particular sensor(s) that provided readings/data that the analysis unit 140 determined to be indicative of water damage and/or intrusion (e.g., the sensor(s) providing data that exceeded a threshold, or providing data that contributed more heavily to a particular output/classification by a neural network, etc.). The notification may list the water damage or intrusion location as a room (e.g., kitchen, basement, etc.), as a structural component (e.g., foundation, roof, etc.), and/or as an appliance or fixture (e.g., dishwasher, bathroom sink, etc.), for example.

In some embodiments, the notification unit 142 generates, and transmits to the user device 110, a report indicating one or more characteristics of the detected or predicted water damage and/or intrusion, including at least a location (e.g., a location of water damage within the structure, or a location where a water intrusion is happening or may likely happen).

In some embodiments, the notification unit 142 (or another component of WDIM application 132) also or instead generates one or more recommendations based upon the determinations/predictions made by the analysis unit 140, and transmits the recommendation(s) to the user device 110 or another device/system in the manner described above (e.g., via a dedicated application on a mobile device of the user). For example, the notification unit 142 may generate a report indicating one or more actions for mitigating or preventing detected/predicted water damage or water intrusion.

In some of these embodiments, the recommended action(s) provide, or are associated with, an insurance discount for the user. For example, the recommended action(s) may include contacting or scheduling an entity (e.g., contractor) to perform a home repair or modification, or home maintenance (e.g., cleaning duct work, inspecting or repairing a ventilation or HVAC system, grading soil outside a foundation of the home, etc.). In some embodiments, the WDIM application 132 (or another application) monitors whether the user performs the recommended action(s) (e.g., by receiving data from the user device 110, such as data indicating whether the user selected an option to contact a particular contractor, or user confirmation that a repair or maintenance job was completed), and causes an insurance discount to be applied for the user (i.e., the user's account or another account that lists the user, etc.) in response to determining that the user performed the recommended action(s).

In alternative embodiments, the notification unit 142 causes some or all notifications to be presented by a display device of computing system 104 (e.g., locally, or at a display of a client device, etc.), or by another computing device or system.

The example WUM application 134 of FIG. 1 includes a modeling unit 150, an analysis unit 152, and a notification unit 154. Generally, the modeling unit 150 processes data indicative of various factors, such as sensor data generated by sensor(s) 102, locally stored/known information (e.g., information relating to home configuration or layout, appliances in the home, number and/or identifiers of different people in the home, etc.), data entered by the homeowner or other user (e.g., information regarding the locations of various fixtures and/or appliances in the home), and/or data from third parties 112 (e.g., weather data, social media data, etc.), in order to determine/identify patterns of water usage in association with (e.g., within and/or in the yard of) the home.

In particular, the modeling unit 150 may build a baseline water usage model by processing any type(s) of sensor and/or other data that is indicative of water usage, such as data from flow sensors (of sensor(s) 102) within respective fixtures (e.g., faucets, pipes) of the home, data from smart appliances (e.g., data indicating when a dishwasher or laundry washing machine is running or has run a cycle, where the cycle is associated with a known amount of water usage), and/or data from an irrigation or automatic pool-fill system (e.g., data from sensors associated with the system, or programming/schedule data provided by a user or a controller of the system, etc.), for example.

Based upon such data, the modeling unit 150 may attribute/associate each instance (water usage event) and amount of water usage to a particular location and/or entity. For example, the modeling unit 150 may build/maintain/populate/update a baseline water usage model that includes a table or other data structure (e.g., in a database stored in memory 130), with the data structure associating locations and/or entities with water usage events and associated information (e.g., time or time range, day of week, and water amount of the water usage event). In other embodiments, the collected raw data itself constitutes the baseline water usage model (e.g., in some embodiments where clustering is used by analysis unit 152 to detect anomalies, as discussed below).

As a more specific example, the modeling unit 150 may receive continuous flow data from a fixture, and generate a table entry when the flow data indicates a flow rate threshold (e.g., a threshold of zero) is surpassed (e.g., the entry "MB_sink/21:14/Mon/1.373" when the sensor indicates that a master bathroom sink faucet output 1.373 gallons at 9:14 pm on a Monday night, or the entry "PF/01:30/Wed/22" when an automatic pool-fill system indicates that 22 gallons were added to a pool at 1:30 am on Wednesday, etc.). Alternatively or additionally, in some embodiments and/or instances, the modeling unit 150 may indicate the person with which a water usage event is associated (e.g., the entry "MB_sink/21:14/Mon/1.373/3" if the modeling unit 150 was able to determine that a family member with the identifier "3" initiated the water usage event, or "MB_sink/21:14/Mon/1.373/0" if the modeling unit 150 was unable to determine who initiated the water usage event).

The modeling unit 150 may build and/or update the baseline water usage model based upon sensor and/or other data for a number of different water sources in and/or around the home (e.g., sinks, bathtubs, showers, toilets, appliances such as dishwashers and laundry washing machines, water heaters, outdoor hose faucets, pools, and/or irrigation systems), and/or for a number of different people in the house (e.g., all family members, or all family members of at least a threshold age). In some embodiments, the modeling unit 150 at some point (e.g., after collecting a threshold amount of data, or after a set time period, etc.) determines that the table or other data structure (or collection of raw data, etc.) may be used as a "final" model of water usage for the house and/or inhabitants, which may then be used by the analysis unit 152 as discussed below. In other embodiments, the modeling unit 150 continues to update or expand the model even after the analysis unit 152 begins to use the model (i.e., specific instances of the model) as discussed below.

The analysis unit 152 uses the baseline water usage model generated by the modeling unit 150 to detect anomalous water usage associated with a particular location and/or entity (e.g., room, area, person, appliance, and/or fixture, etc.) of the home. In particular, the analysis unit 152 may determine whether any received sensor and/or controller data, of the same type(s) as that used to generate the baseline model, is anomalous in view of the baseline model. This may include determining whether each detected water usage event is anomalous (e.g., a shower in a particular bathroom running for an excessive amount of time), and/or determining whether an aggregate of multiple water usage events is anomalous (e.g., the shower being used more than usual on a per-month basis).

The analysis unit 152 generally determines whether event(s) is/are anomalous by comparing to past water usage events, and/or by generating statistics based upon water usage events and comparing to statistics that modeling unit 150 generated based upon past water usage events. For example, the baseline model may indicate that all bathroom sinks in the home, on average, use 28 gallons of water per month, and the analysis unit 152 may determine that water usage is anomalous for a particular bathroom sink (and/or a particular person who uses that sink) if that total is exceeded by more than 20% in a given month (e.g., more than 33.6 gallons per month). As another example, the baseline water usage model may indicate that a particular person took an excessively long shower if the shower time duration was above the 90th percentile of shower durations as reflected in the baseline model. Generally, the analysis unit 152 may use any suitable rules or algorithms (e.g., comparing sensor data values to baseline model values), and/or one or more machine learning models (e.g., a clustering technique incorporating the baseline model data).

In some embodiments, the analysis unit 152 determines whether water usage events associated with a pool (indoor or outdoor) are anomalous, after the modeling unit 150 builds a baseline water usage model (or a portion thereof) for the pool. For example, the baseline model may include an estimated amount of water used per time period (e.g., day, week, etc.) based upon one or more factors, such as a measured fill rate of an automated pool-fill system and/or one or more weather conditions (e.g., temperature, whether overcast or sunny, etc.).

The notification unit 154 generates notifications relating to water usage, and directly or indirectly transmits the notifications to the user device 110 (e.g., via the network interface 122 and network 106, to be presented on a graphical user interface generated by an application executing on the user device 110, or as a text message or email, etc.) for display to the user. For example, the notification unit 154 may cause the user device 110 to present an indication (e.g., alert) when a particular entity (e.g., person, appliance, etc.) is associated with an abnormally high amount of water usage, which may indicate a leak or simply inefficient water usage. The indication may be a statement indicating the entity and the cause of the anomaly (e.g., "Water usage in the second bathroom shower is 43% above usual levels"), for example.

In some embodiments, the notification unit 154 generates, and transmits to the user device 110, a report apportioning water usage (e.g., in terms of statistics such as average daily use, maximum amounts, etc.) to each of multiple locations and/or entities for a given time period (e.g., the previous month, quarter, or year). The report may indicate which members of the household contributed to most to water usage, and how their respective water usage compared to their past water usage (or to the household average, etc.). In some embodiments, the report includes detailed information on water usage by location and/or entity (e.g., person), and indicates or highlights specific locations, entities, and/or instances that were associated with abnormally or disproportionately high amounts of water usage, thereby enabling a homeowner or other user to take targeted, remedial action to increase water usage efficiency in the future.

In some embodiments, the notification unit 154 (or another component of WUM application 134) also or instead generates one or more recommendations for improving water usage efficiency based upon the output of the analysis unit 152, and transmits the recommendation(s) to the user device 110 or another device/system in the manner described above (e.g., via a dedicated application on a mobile device of the user). For example, the notification unit 154 may generate a report indicating one or more actions for improving water usage efficiency, such as replacing or repairing (e.g., with a higher-efficiency model) a dishwasher that was determined by the analysis unit 152 to have unexpectedly high water usage.

In alternative embodiments, the notification unit 154 causes some or all notifications to be presented by a display device of computing system 104 (e.g., locally, or at a display of a client device, etc.), or by another computing device or system.

Exemplary Sensors

Figure 2:
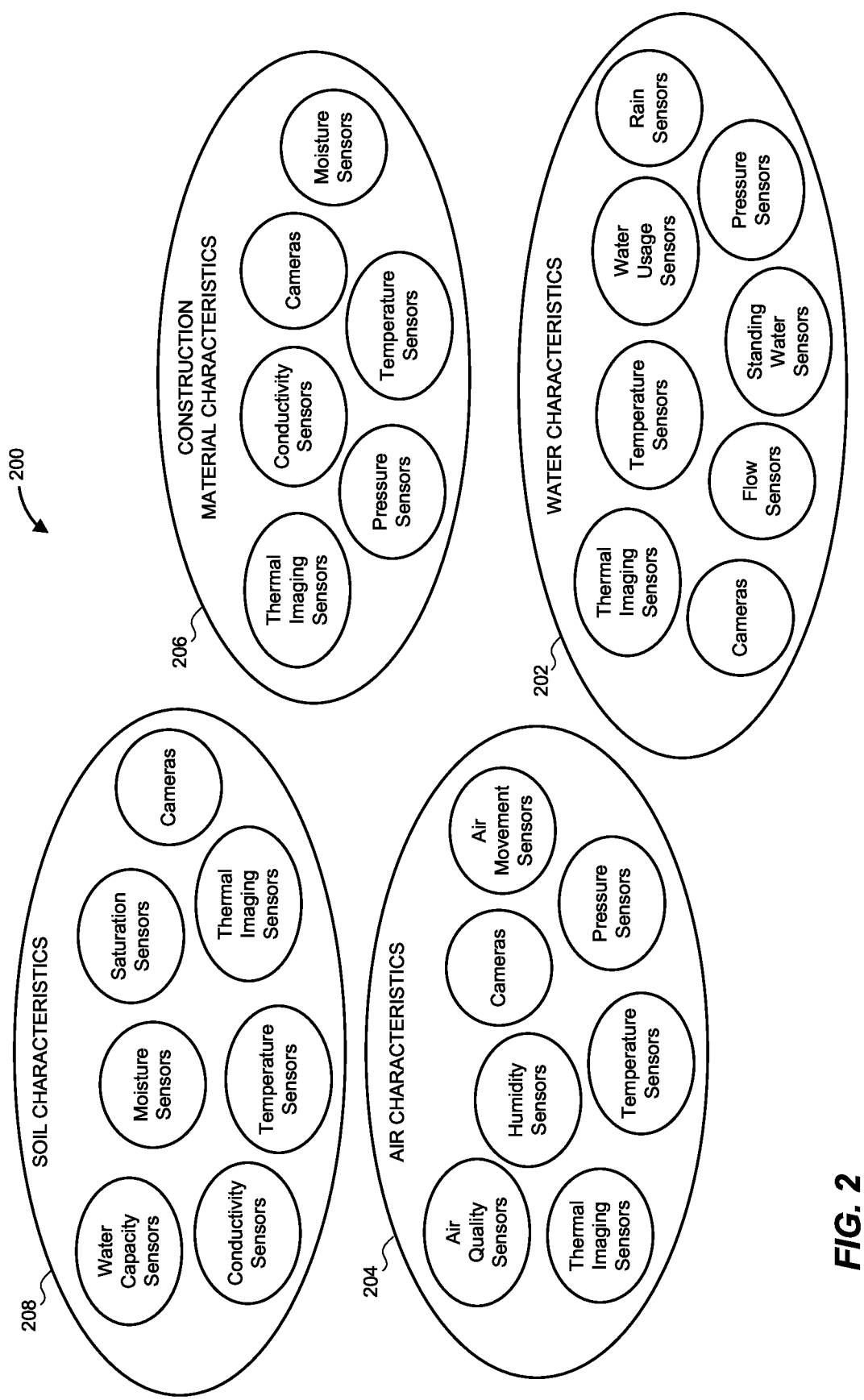
FIG. 2 depicts exemplary types of sensors that may be used in the system in FIG. 1, according to one embodiment.

FIG. 2 depicts exemplary sensor types 200 that may be used in the computer system 100 in FIG. 1, according to one embodiment. As seen in FIG. 2, the sensor types 200 may include sensors 202 that detect characteristics of water, sensors 204 that detect characteristics of air, sensors 206 that detect characteristics of construction materials, and/or sensors 208 that detect characteristics of soil. Other sensor types are also possible, such as sensors that detect energy usage (e.g., and energy usage meter), for example.

The sensors 202 may directly and/or indirectly detect water characteristics. Sensors 202 may include temperature sensors, flow sensors, water usage sensors, thermal imaging sensors, cameras, standing water sensors, water pressure sensors, rain sensors, and/or other suitable sensor types. It is understood that the depicted sensor types may have some overlap. For example, analysis unit 140 and/or analysis unit 152 may use a flow sensor as a water usage sensor, and/or may use cameras and/or thermal imaging sensors to detect rain and/or standing water, etc.

The sensors 204 may directly and/or indirectly detect air characteristics. Sensors 204 may include temperature sensors, air movement sensors, humidity sensors, air quality sensors (e.g., to provide mold and/or other particle counts), thermal imaging sensors, cameras, air pressure sensors, and/or other suitable sensor types. Again, it is understood that the depicted sensor types may have some overlap. For example, analysis unit 140 and/or analysis unit 152 may use thermometers for the temperature sensors, or may instead use the thermal imaging sensors.

The sensors 206 may directly and/or indirectly detect construction material characteristics. The construction materials may be any structural or ornamental components or portion of the home, such as a floorboard, a piece of drywall, a soffit, an eave, a roofing component (shingles, plywood, underlayment, etc.), a rafter, a beam, a window or window frame, a door, and so on. Sensors 206 may be embedded or otherwise incorporated within the construction materials, or may simply be near (e.g., mounted on) or otherwise proximate to the construction materials.

Sensors 206 may include temperature sensors, conductivity sensors, moisture sensors, thermal imaging sensors, cameras, pressure sensors, and/or other suitable sensor types. It is understood that the depicted sensor types may have some overlap. For example, analysis unit 140 and/or analysis unit 152 may use a camera or thermal imaging sensor to detect moisture in wall or floor materials, based upon the visual or thermal appearance of the materials.

The sensors 208 may directly and/or indirectly detect soil characteristics. The soil may be dirt/soil or any other material in or on the ground, such as mulch, sand, etc. Sensors 208 may be on the ground/soil or buried beneath the surface, for example, or placed proximate to the ground/soil (e.g., in the case of a camera).

Sensors 208 may include temperature sensors, saturation sensors, water capacity sensors, conductivity sensors, moisture sensors, thermal imaging sensors, cameras, and/or other suitable sensor types. It is understood that the depicted sensor types may have some overlap. For example, analysis unit 140 and/or analysis unit 152 may use thermometers for the temperature sensors, or may instead use the thermal imaging sensors.

Exemplary Information Types

Figure 3:
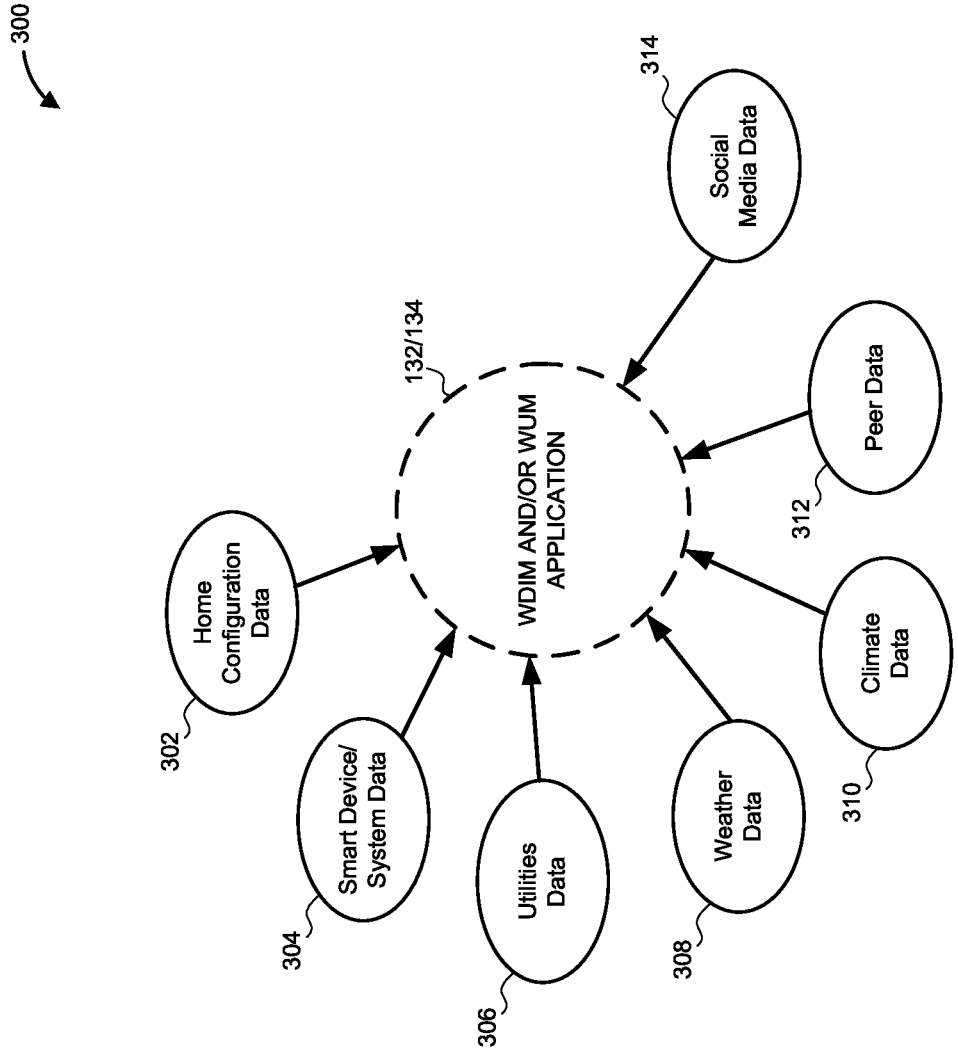
FIG. 3 depicts exemplary types of information that may be provided by the third party systems and/or service(s) and/or other portions of the system in FIG. 1, according to one embodiment.

FIG. 3 depicts exemplary information types 300 that may be provided by the third parties 112 and/or other portions of the system 100 in FIG. 1, according to one embodiment. The information types 300 may be used/analyzed by WDIM application 132 and/or WUM application 134 to make the various determinations, predictions, and/or models discussed herein, for example. In the example shown, the information types 300 include home configuration data 302, smart device/system data 304, utilities data 306, weather data 308, climate data 310, peer data 312, and social media data 314.

The home configuration data 302 may include data representing the arrangement/configuration of at least a portion of the home and/or yard. The data 302 may include, for example, and for each of one or more locations, data indicating how water entering (and/or pooled at) that location will, in the absence of any efforts to contain the water, spread to one or more other locations. For example, the data 302 may include full or partial digital blueprints of the home and/or yard.

As another example, the data 302 may include a map of nodes with directional connections, with each node representing a particular area in the home, and with each directional connection indicating the other node(s)/areas, if any, to which any water at the node will spread if the water is not constrained. As a more specific example, adjacent rooms on the same floor may be linked by a bidirectional connection (to indicate that water will tend to spread from either one to the other), if standing water is present, and a first room above a second room may be linked by a unidirectional connection leading from the first room to the second room (to indicate that gravity will cause the water to go from the first room to the second, but not vice versa).

The home configuration data 302 may be provided by a third party 112, may be entered by a user (e.g., via user device 110), or may be provided in any other suitable way. The analysis unit 140 may use the data 302, after identifying a first area of water damage or water intrusion, to identify one or more additional areas where water damage or water intrusion occurred or may occur.

The smart device/system data 304 may include data provided by any suitable smart device or system (i.e., any suitable device or system with processing power and network communication abilities). The data 304 may include, for example, data sent be a smart dishwasher or refrigerator, and/or data sent by a home security system, an HVAC system, an irrigation system, an automatic pool fill system, and so on. The data 304 may indicate times of operation, water usage amounts or rates, error codes or messages (e.g., indicating a leak), and so on.

The analysis unit 140 may use the data 304 to help determine whether water damage likely occurred in a particular area, for example. As another example, the analysis unit 152 may use the data 304 to assess normal water usage patterns for specific appliances or systems within the home, and/or to identify deviations from the baseline water usage patterns, etc.

The utilities data 306 may include data provided by one or more of sensor(s) 102 (e.g., a water usage meter for the entire home, etc.), and/or data provided by third parties 112 (e.g., monthly water usage data). The analysis unit 152 may use the data 306 to assess normal water usage patterns for the home, and/or to identify deviations from the baseline water usage patterns, for example.

The weather data 308 may include data provided by one or more of sensor(s) 102 (e.g., a rain sensor, a thermometer, etc.), and/or data provided by third parties 112 (e.g., a weather service). The analysis unit 140 may use the data 308 to determine the presence or likelihood of a water intrusion, for example. As another example, the analysis unit 152 may use the data 308 to assess how weather affects water usage patterns for the home, and/or to make predictions of water usage based upon future weather, for example.

The climate data 310 may include data provided by third parties 112, and/or user entered information, for example. The analysis unit 140 may use the data 310 to determine the presence or likelihood of water damage or a water intrusion, and/or the analysis unit 152 may use the data 310 to make predictions of water usage, or to compare water usage to the water usage of other homes in a similar climate, for example.

The peer data 312 may include data provided by third parties 112 (e.g., a service provider that provides and/or operates the computing system 104, and also similar computing systems for many other users), for example. The data 312 may be anonymized aggregate data, and may reflect water damage, water intrusion, and/or water usage data for other users with one or more factors in common with the user or beneficiary of the computing system 124 (e.g., same neighborhood or other geographical area, same climate, etc.). The analysis unit 140 may use the data 312 to determine the likelihood of water damage or a water intrusion (e.g., by increasing the likelihood of a water intrusion if neighbors have experienced a recent water intrusion), and/or the analysis unit 152 may use the data 312 to compare water usage to the water usage of other homes in a similar circumstance (area, climate, etc.), for example.

The social media data 314 may include data provided by third parties 112 (e.g., a social media service provider). The data 314 may be anonymized, and may indicate whether other, similarly situated homes have been subject to recent water damage or water intrusion. The analysis unit 140 may use the data 312 to determine the likelihood of water damage or a water intrusion (e.g., by increasing the likelihood of a water intrusion if neighbors have posted about their experiences with recent water intrusions). The analysis unit 140 may analyze posts from others and use natural language processing (NLP) techniques to determine whether water damage and/or water intrusion events have occurred for others, and may use the timing of the posts to determine the timing of those water damage and/or water intrusion events, for example.

Exemplary Water-Related Incidents

Figure 4:
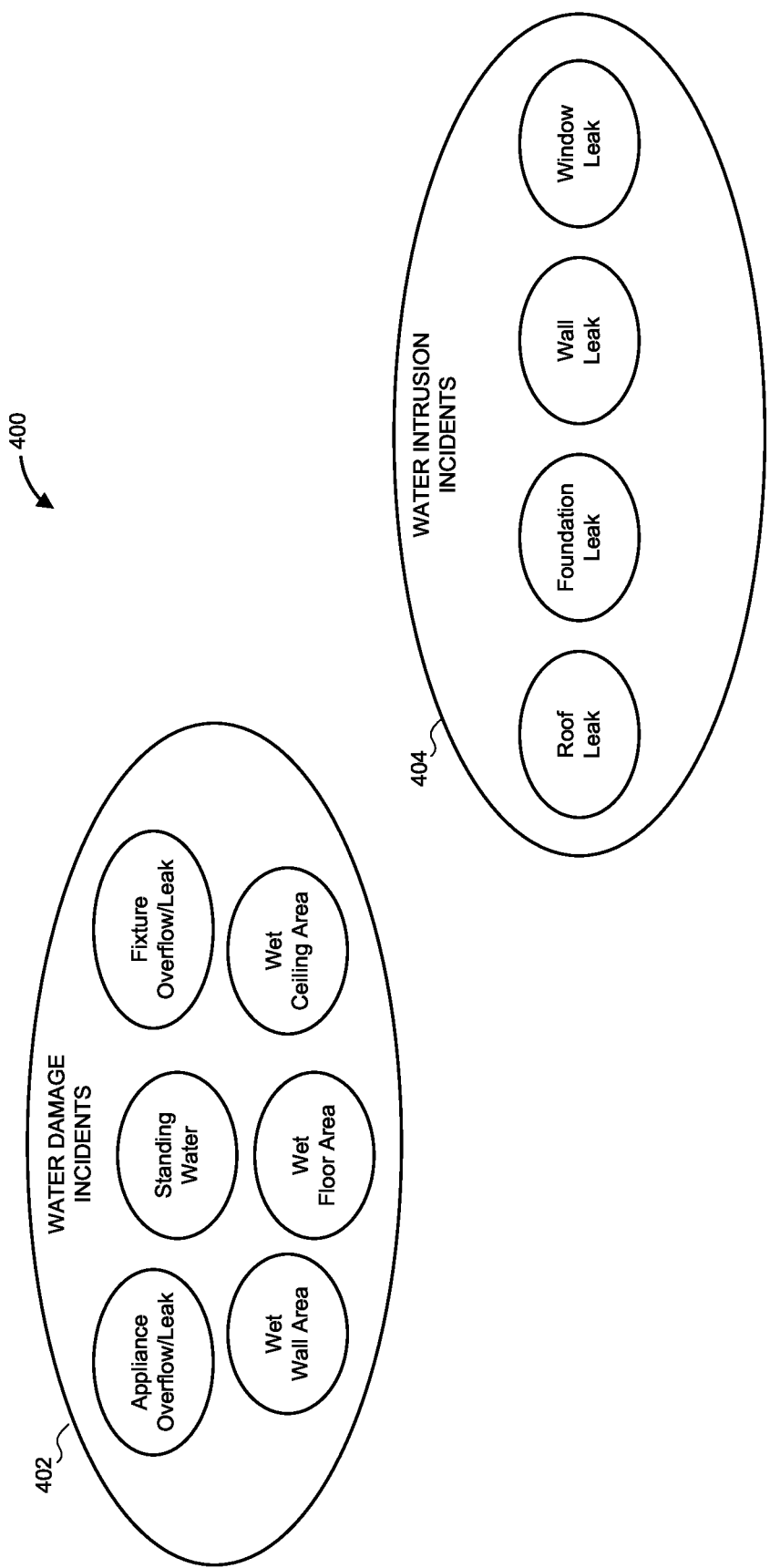
FIG. 4 depicts exemplary water-related incidents that may be identified based upon data from one or more of the sensors of FIG. 1, and/or using one or more of the types of information of FIG. 3, according to one embodiment.

FIG. 4 depicts exemplary water-related incidents 400 that may be identified based upon data from one or more of the sensor(s) 102 of FIG. 1, and/or using one or more of the information types 300 of FIG. 3, according to one embodiment. Generally, the incidents 400 may include water damage incidents 402 and/or water intrusion incidents 404, either or both of which may be detected and/or predicted by the analysis unit 140.

The water damage incidents 402 may include an appliance overflow or leak (e.g., water leaking from the bottom of a dishwasher or laundry washing machine), a fixture overflow or leak (e.g., a stoppered bathtub or sink overflowing or a leak in a faucet or pipe), standing water (e.g., a pool of water), a wet wall area (e.g., wet drywall or paneling), a wet floor area (e.g., carpeting or floor boards that have absorbed water, or the standing water noted above), and/or a wet ceiling area (e.g., wet drywall), for example.

The water intrusion incidents 404 represent incidents in which water intrudes into the home from the external environment. The incidents 404 may include a roof leak, a foundation leak, a wall leak, or a window leak, for example. While the incidents 402 generally correspond to events in which water initially entered the home from an external source (e.g., from a city water reservoir), it is understood that incidents 404 instead represent situations in which water first enters the home in an uncontrolled or undesired manner.

Exemplary Water Damage Prediction & Detection

Figure 5:
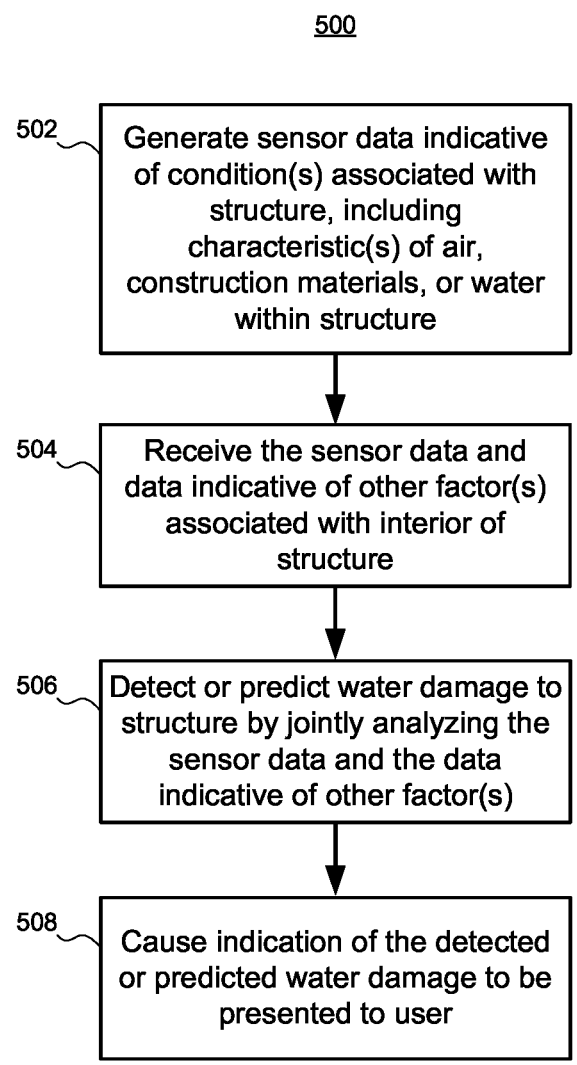
FIG. 5 is a flow chart depicting an exemplary computer-implemented method of detecting or predicting water damage within a structure, according to one embodiment.

FIG. 5 is a flow chart depicting an exemplary computer-implemented method 500 of detecting or predicting water damage within a structure, according to one embodiment. The method 500 may be performed by the sensor(s) 102 and the computing system 104 (e.g., the processing unit 120 when executing the instructions of the WDIM application 132), for example.

In the method 500, sensor data is generated (e.g., by one or more of sensor(s) 102) (block 502). The sensor data may be indicative of one or more conditions associated with a structure, and the condition(s) may include one or more characteristics of water, air, and/or construction materials within the structure (e.g., characteristics 202, 204, and/or 206).

Also in the method 500, the sensor data generated at block 502, and data indicative of one or more other factors associated with the interior of the structure, is received (e.g., by analysis unit 140) (block 504). The other factor(s) may include, for example, one or more known characteristics of the structure (e.g., a presence or absence of water outlets and/or water inlets in a particular area of the structure, a node/connection map as discussed above, a configuration of walls and/or appliances in a particular area of the structure, an absorption rate of walls and/or floors in a particular area of the structure, etc.), and/or factors represented by additional sensor data (e.g., sensor data indicative of characteristic(s) of water, air, and/or construction material(s) comprising the structure). The factor(s) may correspond to data from any sensor types 200 in FIG. 2, and/or to any information types 300 in FIG. 3, for example.

Also in the method 500, water damage to the structure is detected or predicted (e.g., by analysis unit 140) (block 506). Block 506 may include jointly analyzing the sensor data, and the data indicative of the other factor(s), received at block 504.

And indication of the detected or predicted water damage is caused (e.g., by notification unit 142 or notification unit 154) to be presented to a user (e.g., an operator of user device 110) (block 508). Block 508 may include displaying the indication, or sending data to another computing device or system (e.g., to user device 110) to cause the other device or system to present the indication (e.g., via a screen or other display of user device 110).

Figure 6:
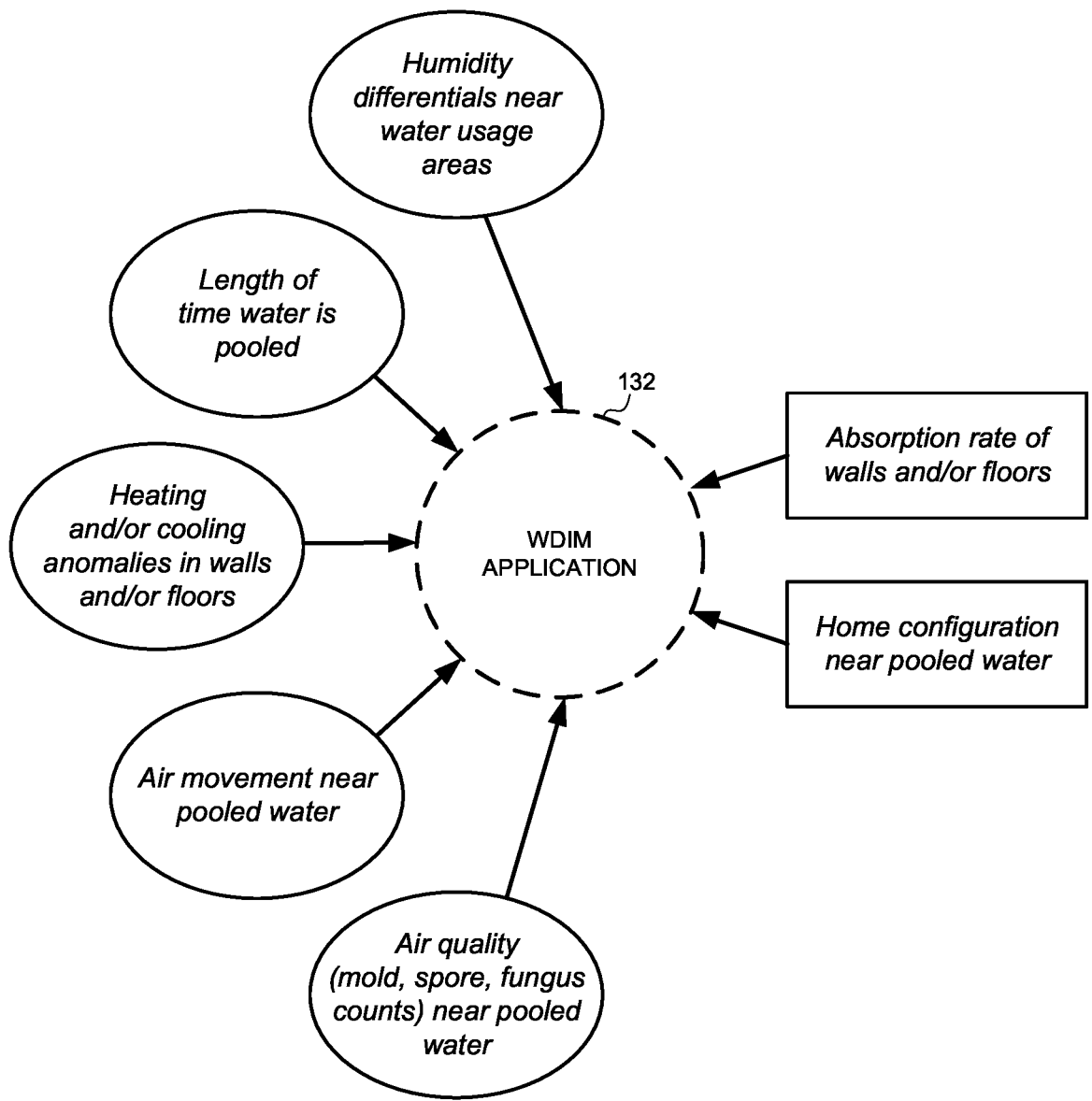
FIG. 6 depicts exemplary input information for identifying or predicting water damage in a home or other structure, according to one embodiment.

FIG. 6 depicts input information 600 for identifying or predicting water damage in a home or other structure, according to one example embodiment. The input information 600 may be input to WDIM application 132, for processing by the analysis unit 140 to implement blocks 504 and 506 of the method 500, for example.

In this example, the input information 600 includes various measured inputs, including humidity differentials near known water usage areas (e.g., as measured by humidity sensors of sensors 204), the length of time water is pooled (e.g., based upon time stamps associated with measurements by a standing water sensor of sensors 202), heating and/or cooling anomalies in walls and/or floors (e.g., based upon a baseline model and temperature measurements by temperature sensors or thermal imaging sensors of sensors 206), air movement near pooled water (e.g., as measured by air movement sensors of sensors 204), and air quality (e.g., mold, spore, and/or fungus counts) near pooled water (e.g., as measured by air quality sensors of sensors 204). The example input information 600 also includes various known or pre-determined inputs, including the absorption rate of one or more walls and/or floors, and the configuration of the home near the pooled water (e.g., as represented by the node/connection map discussed above).

Exemplary Water Intrusion Prediction & Detection

Figure 7:
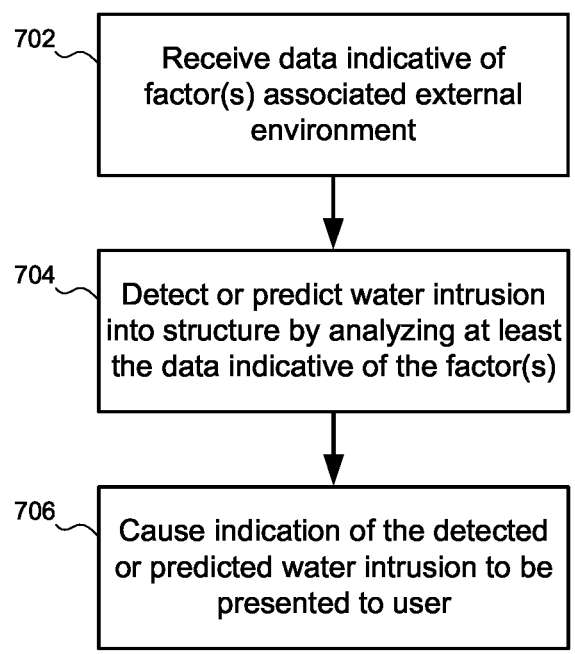
FIG. 7 is a flow chart depicting an exemplary computer-implemented method of detecting or predicting water intrusion into a structure from an external environment, according to one embodiment.

FIG. 7 is a flow chart depicting an exemplary computer-implemented method 700 of detecting or predicting water intrusion into a structure from an external environment, according to one embodiment. The method 700 may be performed by the computing system 104 (e.g., the processing unit 120 when executing the instructions of the WDIM application 132), for example.

In the method 700, data indicative of one or more factors associated with an environment external to the structure is received (e.g., by analysis unit 140) (block 702). The factor(s) may include, for example: (1) water capacity, conductivity, and/or saturation of soil; (2) snow, rain, and/or standing water outside the structure (e.g., based upon camera images); (3) irrigation of land outside the structure (e.g., based upon a programmed irrigation schedule); (4) weather and/or climate data; and/or (5) known water intrusions, or the lack thereof, in one or more other structures in a same area as the structure. Other factors that are also analyzed may include, for example, one or more known or sensed (e.g., by sensor(s) embedded in the foundation construction materials) characteristics of a foundation of the structure, standing water within the structure (e.g., as sensed by one of sensors 202), a configuration of the structure (e.g., whether the structure includes a basement), and/or an amount of time or a percentage of time that at least a portion of a foundation of the structure is wet and/or water is entering the structure through the foundation. The factor(s) may correspond to data from any sensor types 200 in FIG. 2, and/or to any information types 300 in FIG. 3, for example.

Also in the method 700, water intrusion into the structure is detected or predicted (e.g., by analysis unit 140) (block 704), by analyzing at least the data indicative of the factor(s).

Also in the method 700, an indication of the detected or predicted water intrusion is caused (e.g., by notification unit 142 or notification unit 154) to be presented to a user (e.g., an operator of user device 110) (block 706). Block 706 may include displaying the indication, or sending data to another computing device or system (e.g., to user device 110) to cause the other device or system to present the indication (e.g., via a screen or other display of user device 110).

Figure 8:
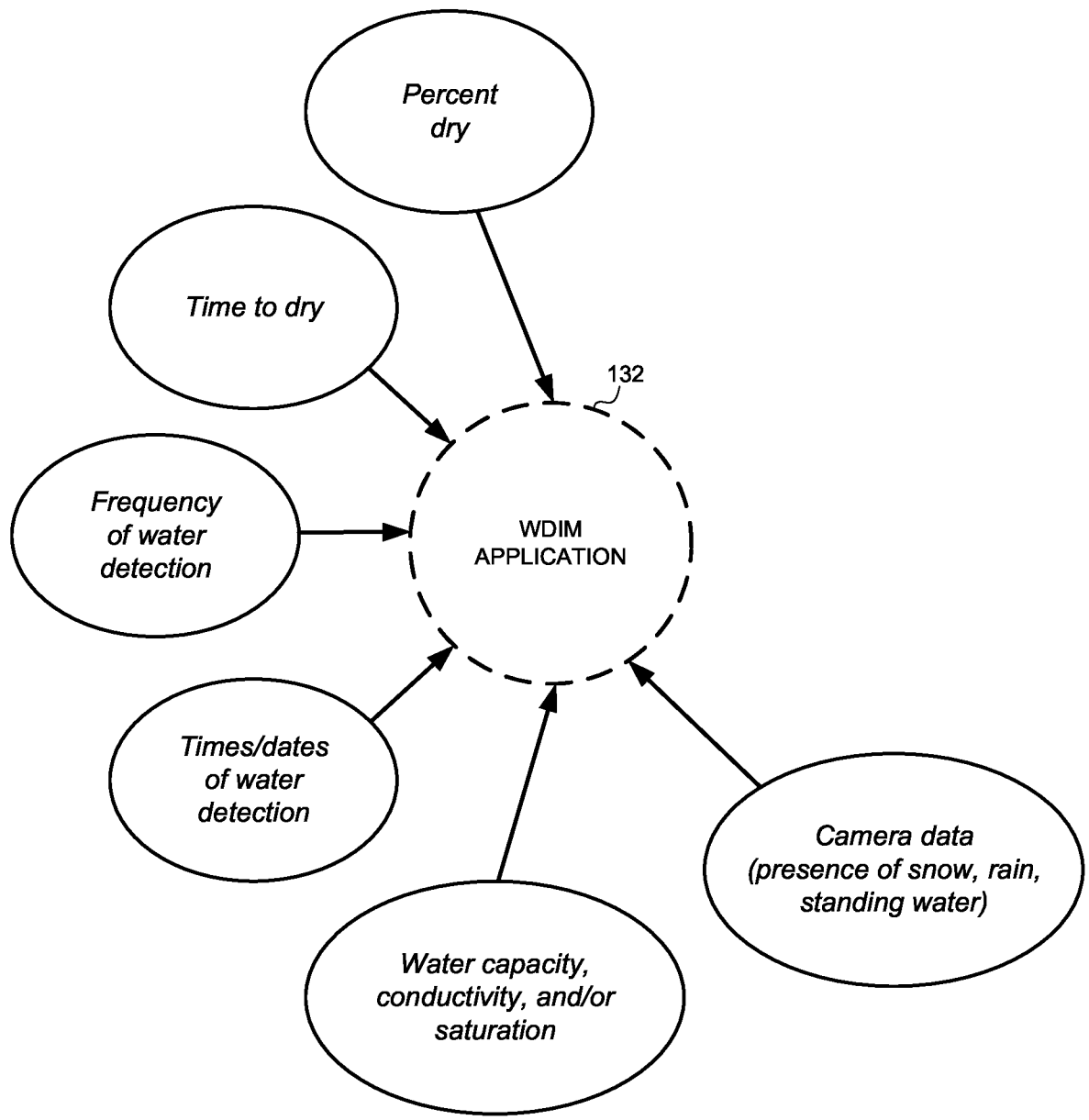
FIG. 8 depicts exemplary input information for identifying or predicting water intrusion into a home or other structure, according to one embodiment.

FIG. 8 depicts input information 800 for identifying or predicting water intrusion into a home or other structure, according to one example embodiment. The input information 800 may be input to WDIM application 132, for processing by the analysis unit 140 to implement blocks 702 and 704 of the method 700, for example.

In this example, the input information 800 includes various measured inputs, including the percentage of a certain area that is dry, the time it takes the area to dry, the frequency at which water is detected in an outdoor area proximate to a home, the times and/or dates of water detection (e.g., the seasons in which water is detected) in the outdoor area, water capacity, conductivity, and/or saturation in the outdoor area, and camera data representing images of the outdoor area (e.g., to show standing water, snow, rain). The WDIM application 132 may also receive, or determine, associated information, such as the time it takes for standing water to drain from the area. The analysis unit 152 may detect or predict water intrusions based upon the input information 800, possibly in combination with other information (e.g., sensed humidity in a basement).

Exemplary Water Usage Monitoring

Figure 9:
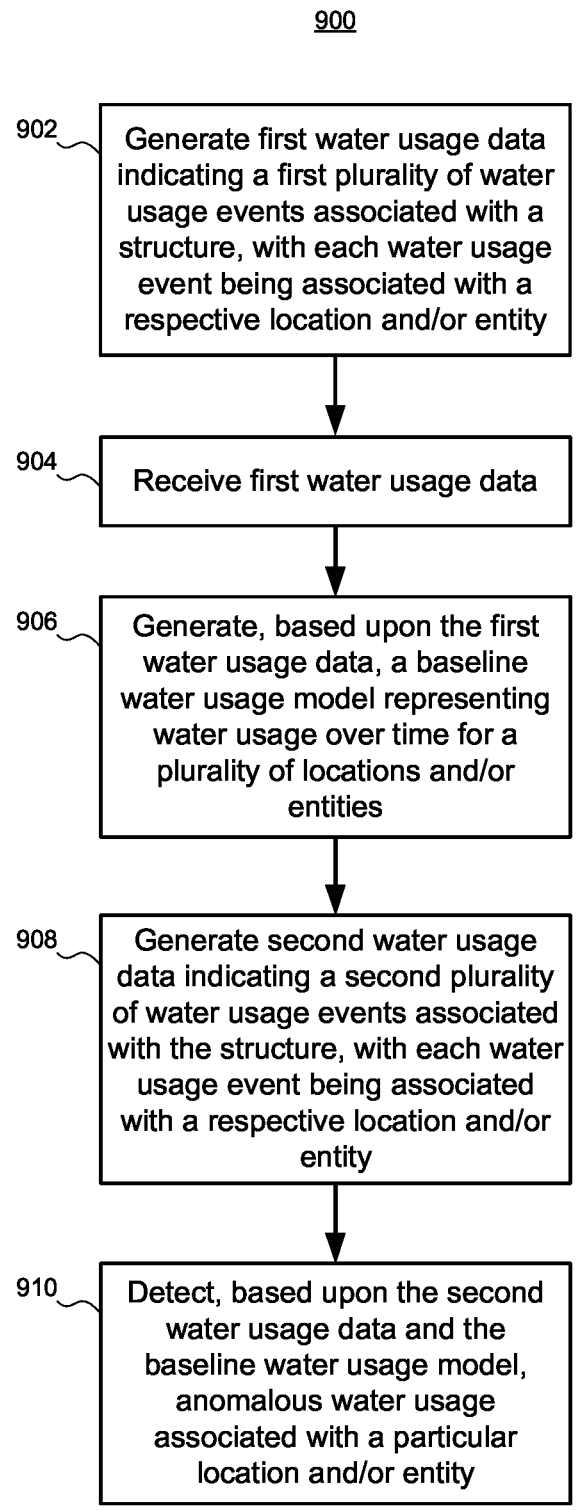
FIG. 9 is a flow chart depicting an exemplary computer-implemented method of monitoring water usage, according to one embodiment.

FIG. 9 is a flow chart depicting an exemplary computer-implemented method 900 of monitoring water usage, according to one embodiment. The method 900 may be performed by the sensor(s) 102, controllers of one or more devices or systems, and/or the computing system 104 (e.g., the processing unit 120 when executing the instructions of the WUM application 134), for example.

In the method 900, first water usage data is generated (e.g., by one or more of sensor(s) 102 and/or one or more controllers) (block 902). The first water usage data may be indicative of a first plurality of water usage events associated with a structure, and each water usage event may be associated with a respective location (e.g., room, area, etc.) and/or entity (e.g., inhabitant/person, fixture, appliance, etc.) of a plurality of locations and/or entities.

Also in the method 900, the first water usage data is received (e.g., by analysis unit 152) (block 904), and, based upon the first water usage data, a baseline water usage model is generated (e.g., by analysis unit 152) (block 906). The baseline water usage model represents water usage over time for the plurality of locations and/or entities.

Also in the method 900, second water usage data is generated (e.g., by the same sensor(s) 102 and/or controller(s) as in block 902) (block 906). The second water usage data may be indicative of a second plurality of water usage events associated with the structure, with each water usage event being associated with a respective location (e.g., room, area, etc.) and/or entity (e.g., inhabitant/person, fixture, appliance, etc.) of the plurality of locations and/or entities.

Also in the method 900, anomalous water usage associated with a particular location and/or entity is detected (e.g., by the analysis unit 152) based upon the second water usage data and the baseline water usage model.

Figure 10:
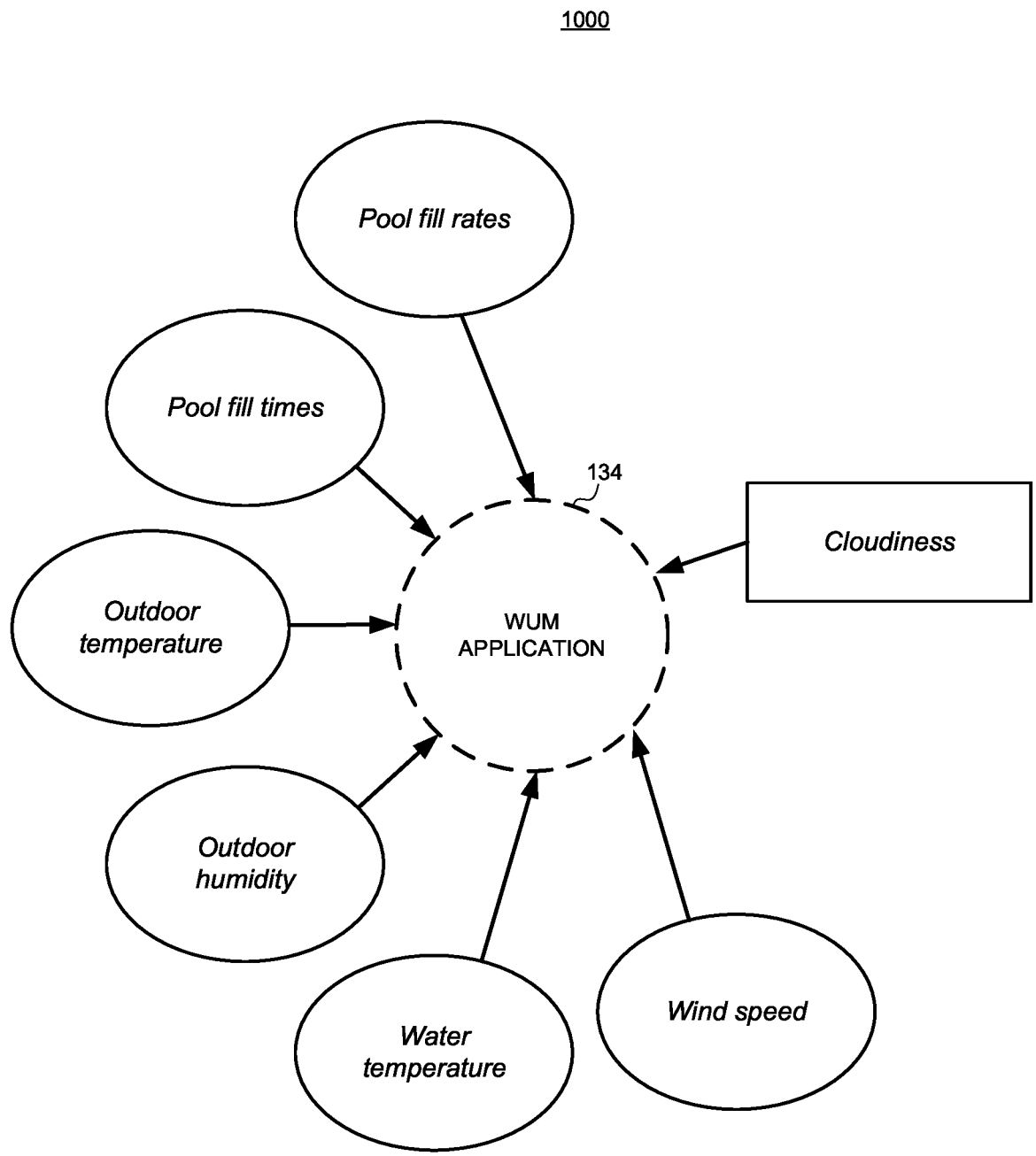
FIG. 10 depicts exemplary input information for measuring the rate of evaporation in a pool, according to one embodiment.

FIG. 10 depicts exemplary input information 1000 for the measuring the rate of evaporation in a pool, according to one embodiment. In some embodiments, the input information 1000 is input to WUM application 134, for processing by the analysis unit 152.

In this example, the input information 1000 includes various measured inputs, including pool fill rates and fill times (e.g., as indicated by a controller of an automatic pool fill system), the outdoor temperature, humidity, and wind speed, and the water temperature. The example input information 1000 may also include one or more known or pre-determined inputs, such as the level of cloudiness or whether it is generally a cloudy day (e.g., as indicated by a weather service of third parties 112). The analysis unit 152 may use the input information 1000 to predict water usage for an automated pool fill system over a particular time period (e.g., to determine a baseline/normal level of pool water usage per day, per week, etc., and/or to identify anomalous water usage over similar time periods), for example.

Exemplary Water Damage Detection Using Energy Harvesting Sensors

Figure 11:
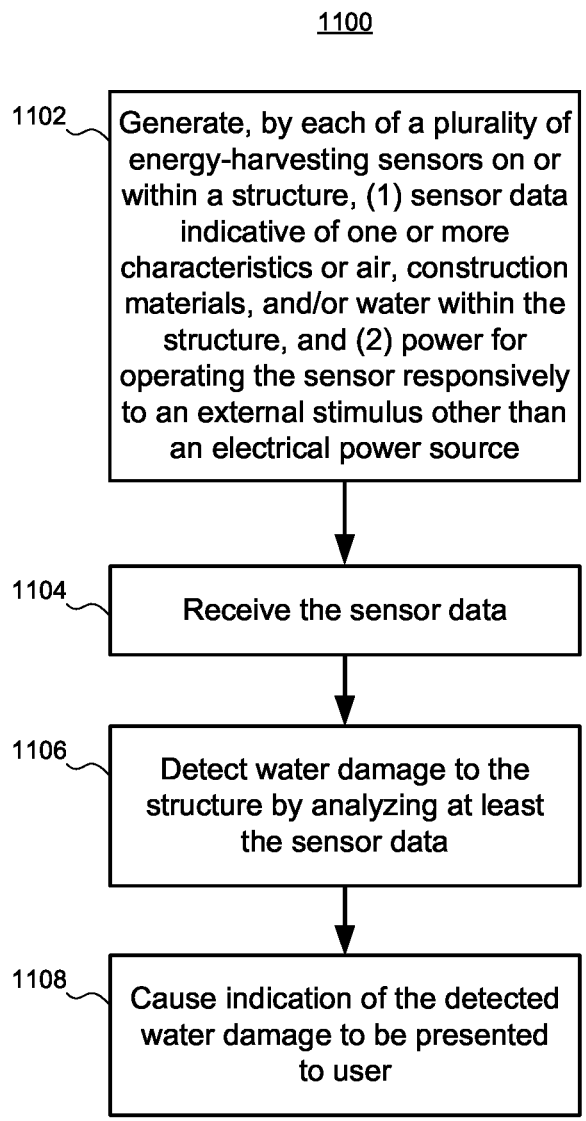
FIG. 11 is a flow chart depicting an exemplary computer-implemented method of detecting water damage to a structure using energy-harvesting sensors, according to one embodiment.

FIG. 11 is a flow chart depicting an exemplary computer-implemented method 1100 of detecting water damage to a structure using energy-harvesting sensors, according to one embodiment. The method 1100 may be performed by the sensor(s) 102 and/or the computing system 104 (e.g., the processing unit 120 when executing the instructions of the WDIM application 134), for example.

The method 1100 may include generating, by each of a plurality of energy-harvesting sensors on or within a structure, sensor data indicative of one or more characteristics or air, construction materials, and/or water within the structure, and power for operating the sensor responsively to an external stimulus other than an electrical power source (block 1102). In other embodiments, block 1102 includes generating the power responsively to a wireless RF signal, such as a WiFi signal, as discussed above.

The method 1100 also includes receiving the sensor data (e.g., by analysis unit 140 or analysis unit 152) (block 1104), and detecting water damage to the structure by analyzing at least the sensor data (block 1106).

The method 1100 also includes causing (e.g., by notification unit 142 or notification unit 154) an indication of the detected water damage to be presented to a user (e.g., an operator of user device 110) (block 1108). Block 1108 may include displaying the indication, or sending data to another computing device or system (e.g., to user device 110) to cause the other device or system to present the indication (e.g., via a screen or other display of user device 110).

Exemplary Smart Water Delivery System

Figure 12:
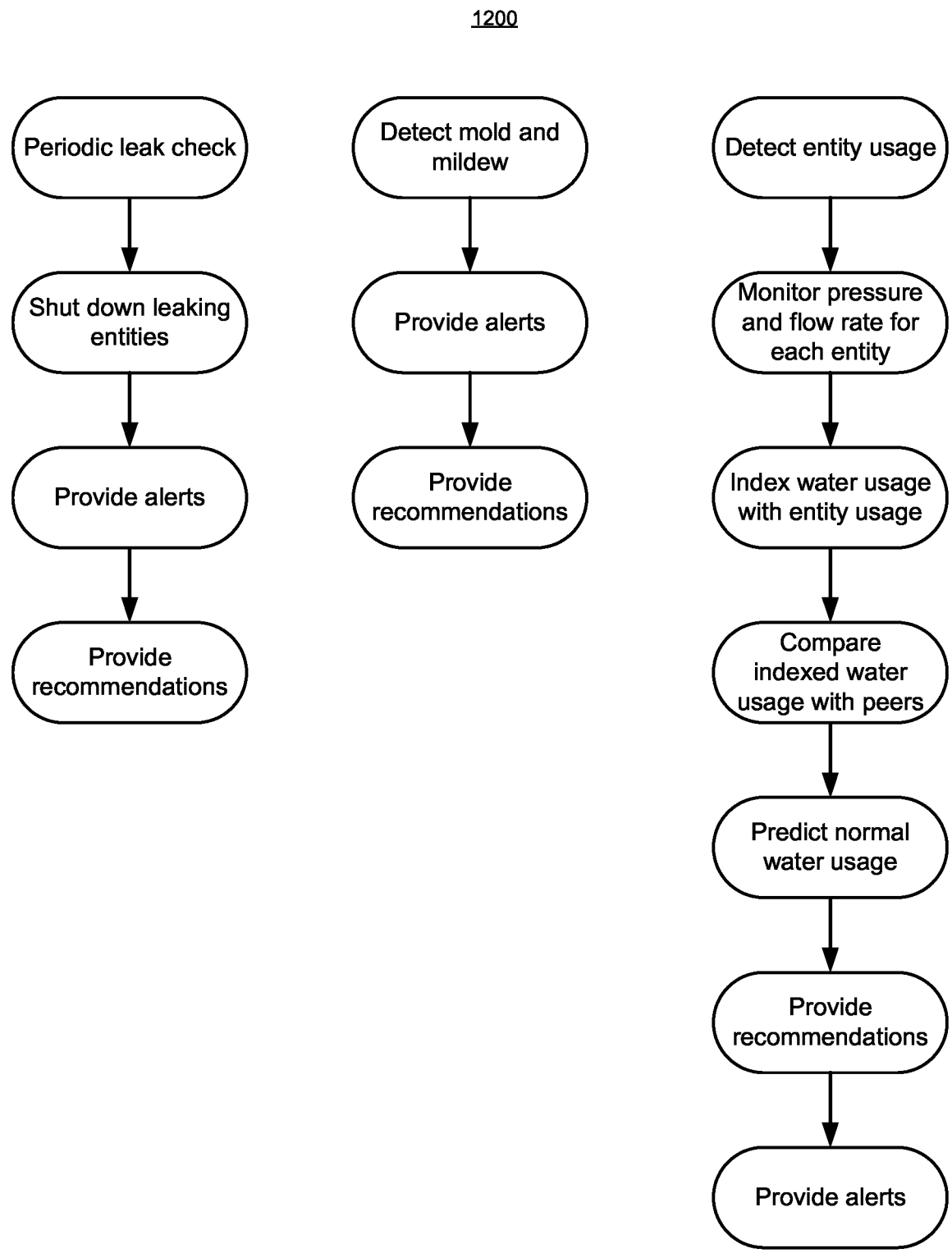
FIG. 12 is a block diagram of depicting exemplary functionality of a smart water delivery system, according to one embodiment.

FIG. 12 is a block diagram of depicting exemplary functionality 1200 of a smart water delivery system, according to one embodiment. The smart water delivery system may include the computing system 104 and sensor(s) 102 (and possibly at least a portion of the network 106), for example.

In the depicted example, the functionality 1200 includes three general categories of features. In a first category, the smart water delivery system may periodically check for leaks. For example, the system may periodically run a "no flow" cycle for appliances, fixtures, and/or other entities (e.g., by shutting down appliance subsystems, or otherwise causing the subsystem(s) to enter a mode of operation in which water flow is not expected, and detecting whether there is still a flow of water to the appliance). The system may also, in some embodiments, shut down any entities (appliances, etc.) for which a leak is detected, and/or cut off a flow of water to any leaking entities. The system may also provide alerts, and/or recommendations for mitigating and/or repairing damage relating to detected leaks.

In a second category, the smart water delivery system may detect mold and mildew (and/or other contaminants such as pollen, fungus, etc.). If detected, the smart water delivery system may provide alerts, and/or recommendations for improving air quality and/or repairing water damage that may have triggered the mold and mildew.

In a third category, the smart water delivery system may detect usage of or by particular entities (e.g., fixtures, appliances, household inhabitants, etc.), and monitor the pressure and/or flow rate over time for each such entity. The system may also index the water usage with the entity usage to determine baseline or "normal" usage rates on a per-entity basis. Further, the system may compare the indexed water usage with peers (e.g., water usage for similar entities in households that are located, in the same neighborhood, occupied by families of a similar size and/or having similar demographics, etc).

The smart water delivery system may also predict baseline/normal water usage (e.g., overall, and/or per entity), and/or may provide recommendations and/or actionable insights (e.g., tips to manage water usage, replace inefficient appliances, or fix leaks, and/or specific areas to target, etc.) and/or alerts (e.g., notifications to homeowner, renter, landlord, short-term host, vacationer, etc.) when baseline water usage norms are exceeded, etc.

Exemplary Damage Prediction & Detection Embodiments

In one aspect, a computer-implemented method of detecting or predicting water damage may be provided. The method may include: (i) generating, via one or more home-mounted or other sensors, home (or interior) air or environmental data; (ii) receiving, via one or more local or remote processors and/or associated transceivers, the home air or environmental data; (iii) analyzing, via the one or more local or remote processors, the home air or environmental data to detect or other determine (1) one or more deteriorating trends in home air quality or condition(s), (2) a home air quality threshold being met or exceeded, (3) a home air quality count being met or exceeded, (4) home or interior airborne particle counts meeting or exceeding a threshold, (5) a temperature or pressure differential meeting or exceeding a threshold, or (6) a home (or interior) air quality or home (or interior) air quality metric or measurement departing or deviating from a baseline or baseline model; (iv) generating and transmitting, via the one or more local or remote processors and/or a transceivers, an alert to a mobile device of a home owner or home occupant; (v) generating and transmitting, via the one or more local or remote processors and/or a transceivers, one or more corrective actions to the mobile device of a home owner or home occupant; and/or (vi) generating and transmitting, via the one or more local or remote processors and/or a transceivers, a report detailing current and/or past home air quality to the mobile device of a home owner or home occupant. The method may include additional, less, or alternate functionality, including that discussed elsewhere herein.

For instance, the one or more home-mounted sensors may be air quality sensors, mold, spore, or fungus sensors. The one or more home-mounted sensors may be humidity sensors or temperature sensors. Additionally or alternatively, the one or more home-mounted sensors may be embedded within construction material of the home.

The one or more corrective actions may provide, or may be associated with, an insurance discount for the homeowner. The method may include (1) monitoring, via the one or more local or remote processors, whether the homeowner follows the one or more corrective actions, and (2) providing, via the one or more local or remote processors, a homeowners or other insurance discount for the homeowner. Additionally or alternatively, the one or more corrective actions may provide, or may be associated with, (1) identifying a contractor or other entity to perform the corrective actions and/or (2) scheduling a time for the contractor or other entity to perform the corrective action (such as clean duct work, repair ventilation or HVAC system, etc.).

In another aspect, a computer system configured to detect or predict home or structure water damage may be provided. The computer system may include one or more home-mounted or other sensors configured to generate home (or interior) air or environmental data; and one or more local or remote processors and/or associated transceivers in wired or wireless communication (such as over one or more radio frequency links) with the one or more home-mounted or other sensors, and configured to: (1) receive the home air or environmental data from the one or more home-mounted or other sensors; (2) analyze the home air or environmental data to detect or other determine (i) one or more deteriorating trends in home air quality or condition(s), (ii) a home air quality threshold being met or exceeded, (iii) a home air quality count being met or exceeded, (iv) home or interior airborne particle counts meeting or exceeding a threshold, (v) a temperature or pressure differential meeting or exceeding a threshold, and/or (vi) a home (or interior) air quality or home (or interior) air quality metric or measurement departing or deviating from a baseline or baseline model; (3) generate and transmit an alert to a mobile device of a home owner or home occupant; (4) generate and transmit one or more corrective actions to the mobile device of a home owner or home occupant; and/or (5) generate and transmit a report detailing current and/or past home air quality to the mobile device of a home owner or home occupant. The system may include additional, less, or alternate functionality, including that discussed elsewhere herein.

For instance, the one or more home-mounted sensors may be air quality sensors, mold, spore, or fungus sensors. Additionally or alternatively, the one or more home-mounted sensors may be humidity sensors or temperature sensors. The one or more home-mounted sensors may be embedded within construction material of the home.

The one or more corrective actions may provide, or may be associated with, an insurance discount for the homeowner. The one or more local or remote processors and/or associated transceivers may be further configured to (1) monitor, or otherwise determine, whether the homeowner follows the one or more corrective actions, and (2) provide a homeowners or other insurance discount for the homeowner.

The one or more local or remote processors and/or associated transceivers may be further configured to (1) identify a contractor or other entity to perform the one or more corrective actions, and/or (2) schedule a time for the contractor or other entity to perform the one or more corrective action (such as clean duct work, repair ventilation or HVAC system, repair or replace sensors or other electronic components, etc.).

Exemplary Water Usage Modeling Embodiments

In one aspect, a computer-implemented method of modeling home water usage may be provided. The method may include: (1) identifying, via one or more local or remote processors, transceivers, or sensors, (i) a water-usage event, (ii) water flowing within a home, and/or (iii) a source of water within the home being operated (such as identifying dish washer; clothes washer; kitchen or bedroom faucet; or shower); (2) identifying, via the one or more local or remote processors, transceivers, or sensors, a specific individual (such as a family or household member) that initiated the water-usage event or the water to flow or the source of water (such as by operating a dish or clothes washer, or kitchen or bedroom faucet, etc.), or determining, via the one or more local or remote processors, transceivers, or sensors, the specific individual is in the vicinity of the source of water or in the same room as the source of water flow (e.g., determine which individual is (i) in the kitchen when the dish washer or kitchen faucet is operated, (ii) in the laundry room of the home when the clothes dryer is operated, (iii) on the second floor of a house when the second floor shower is being used, or (iv) in the master bedroom when the master bedroom faucet or shower is being used); (3) measuring, via the one or more local or remote processors, transceivers, or sensors, an amount of water used during or by the water-usage event or the like; (4) attributing, via the one or more local or remote processors, transceivers, or sensors, the amount of water used to the specific individual identified as initiating the water-usage event; (5) generating and transmitting, via the one or more local or remote processors, transceivers, or sensors, an alert to the mobile device of a home owner when the amount of water used during the water-usage event exceeds a pre-determined amount or lasts over a pre-determined amount of time; and/or (6) generating and transmitting, via the one or more local or remote processors, transceivers, or sensors, an electronic report of household water usage to the mobile device of the home owner, the electronic report of household water usage detailing the amount of water usage of each individual within the household or family by type (clothes washer, dish washer, shower, etc.) and amount for a given period of time (e.g., daily, weekly, monthly, quarterly, etc.). The method may include additional, less, or alternate functionality, including that discussed elsewhere herein.

In another aspect, a computer system configured for modeling home water usage may be provided. The computer system may include one or more local or remote processors, transceivers, and/or sensors configured to: (1) identify (i) a water-usage event within a home, (ii) water flowing within a home, and/or (iii) a source of water within the home being operated (such as identifying dish washer; clothes washer; kitchen or bedroom faucet; or shower); (2) identify a specific individual (such as a family or household member) that initiated the water-usage event or the water to flow or the source of water (such as by operating a dish or clothes washer, or kitchen or bedroom faucet, etc.), or determine the specific individual is in the vicinity of the source of water or in the same room as the source of water flow (e.g., determine which individual is (i) in the kitchen when the dish washer or kitchen faucet is operated, (ii) in the laundry room of the home when the clothes dryer is operated, (iii) on the second floor of a house when the second floor shower is being used, or (iv) in the master bedroom when the master bedroom faucet or shower is being used); (3) measure an amount of water used during or by the water-usage event or the like; (4) attribute the amount of water used to the specific individual identified as initiating the water-usage event; (5) generate and transmit an alert to the mobile device of a home owner when the amount of water sed during the water-usage event exceeds a pre-determined amount or lasts over a pre-determined amount of time; and/or (6) generate and transmit an electronic report of household water usage to the mobile device of the home owner, the electronic report of household water usage detailing the amount of water usage of each individual within the household or family by type (clothes washer, dish washer, shower, etc.) and amount for a given period of time (e.g., daily, weekly, monthly, quarterly, etc.). The system may include additional, less, or alternate functionality, including those discussed elsewhere herein.

Exemplary Aspects

In one aspect, a computer system for detecting water damage to a structure may be provided. The system may include a plurality of energy-harvesting sensors on or within the structure, wherein each sensor of the plurality of energy-harvesting sensors may be configured to (i) generate sensor data indicative of one or more characteristics of air, construction materials, and/or water within the structure, and/or (ii) generate power for operating the sensor responsively to an external stimulus other than an electrical power source; one or more processors; and one or more memories storing instructions that, when executed by the one or more processors, cause the one or more processors to perform a method including (1) receiving sensor data generated by the plurality of energy-harvesting sensors; (2) detecting water damage to the structure by analyzing at least the sensor data; and/or (3) causing an indication of the detected water damage to be presented to a user. The system may include additional, less, or alternate functionality, including that discussed elsewhere herein.

For instance, the plurality of energy-harvesting sensors may include one or more sensors each configured to generate power for operating the sensor responsively to water flowing past the sensor. The one or more sensors may be positioned within one or more pipes or fixtures of the structure. Additionally or alternatively, the plurality of energy-harvesting sensors may include one or more sensors each (i) comprising a material configured to expand when becoming wet and/or (ii) configured to generate power for operating the sensor responsively to the material expanding. Additionally or alternatively, the plurality of energy-harvesting sensors may include one or more sensors each (i) comprising one or more solar cells, and/or (ii) configured to generate power for operating the sensor responsively to the one or more solar cells collecting solar energy. Additionally or alternatively, the plurality of energy-harvesting sensors may include one or more sensors each of which is configured to generate power for operating the sensor responsively to a temperature differential across two regions of the sensor.

In some embodiments, the one or more sensors may be positioned proximate to a water heater within the structure. In other embodiments, the plurality of energy-harvesting sensors may include one or more energy-harvesting sensors embedded within construction materials of the structure.

The sensor data may be indicative of at least one characteristic of air within the structure, the at least one characteristic of air including one or more of: air temperature; air humidity; air movement; or airborne particle count. Additionally or alternatively, the sensor data may be indicative of at least one characteristic of construction materials within the structure, the at least one characteristic of construction materials including or more of: moisture of the construction materials; or impedance of the construction materials. Additionally or alternatively, the sensor data may be indicative of at least one characteristic of water within the structure, the at least one characteristic of water including or more of: a presence of pooled water within the structure; or a flow of water within the structure.

Causing the indication of the detected water damage to be presented to the user may include generating an alert; and/or transmitting the alert to a device of the user. Transmitting the alert may include causing an application executing on a mobile device of the user to display the alert. The alert may include a report indicating one or more characteristics of the detected water damage, including at least a location of the detected water damage within the structure.

In another aspect, a computer-implemented method for detecting water damage to a structure may be provided. The computer-implemented method may include: (1) receiving sensor data generated by a plurality of energy-harvesting sensors on or within the structure, wherein each sensor of the plurality of energy-harvesting sensors is configured to (i) generate sensor data indicative of one or more characteristics of air, construction materials, and/or water within the structure, and/or (ii) generate power for operating the sensor responsively to an external stimulus other than an electrical power source; (2) detecting water damage to the structure by analyzing at least the sensor data; and/or (3) causing an indication of the detected water damage to be presented to a user. The method may include additional, less, or alternate functionality and actions, including those discussed elsewhere herein.

For instance, the plurality of energy-harvesting sensors may include one or more sensors each configured to generate power for operating the sensor responsively to water flowing past the sensor. In some embodiments, the one or more sensors may be positioned within one or more pipes or fixtures of the structure. Additionally or alternatively, the plurality of energy-harvesting sensors may include one or more sensors each (i) comprising a material configured to expand when becoming wet, and/or (ii) configured to generate power for operating the sensor responsively to the material expanding. Additionally or alternatively, the plurality of energy-harvesting sensors may include one or more sensors each (i) comprising one or more solar cells and (ii) configured to generate power for operating the sensor responsively to the one or more solar cells collecting solar energy. Additionally or alternatively, the plurality of energy-harvesting sensors may include one or more sensors each of which is configured to generate power for operating the sensor responsively to a temperature differential across two regions of the sensor. In some embodiments, the one or more sensors may be positioned proximate to a water heater within the structure. Additionally or alternatively, the plurality of energy-harvesting sensors may include one or more energy-harvesting sensors embedded within construction materials of the structure.

In certain embodiments, the sensor data may be indicative of at least one characteristic of air within the structure, the at least one characteristic of air including one or more of: air temperature; air humidity; air movement; or airborne particle count. Additionally or alternatively, the sensor data may be indicative of at least one characteristic of construction materials within the structure, the at least one characteristic of construction materials including or more of: moisture of the construction materials; or impedance of the construction materials. Additionally or alternatively, the sensor data may be indicative of at least one characteristic of water within the structure, the at least one characteristic of water including or more of: a presence of pooled water within the structure; or a flow of water within the structure.

Causing the indication of the detected water damage to be presented to the user may include generating an alert; and/or transmitting the alert to a device of the user. Transmitting the alert may include causing an application executing on a mobile device of the user to display the alert. The alert may include a report indicating one or more characteristics of the detected water damage, including at least a location of the detected water damage within the structure.

In another aspect, one or more tangible, non-transitory, computer-readable media storing instructions that, when executed by one or more processors, cause the one or more processors to: (1) receive sensor data generated by a plurality of energy-harvesting sensors on or within the structure, wherein each sensor of the plurality of energy-harvesting sensors is configured to (i) generate sensor data indicative of one or more characteristics of air, construction materials, and/or water within the structure, and/or (ii) generate power for operating the sensor responsively to an external stimulus other than an electrical power source; (2) detect water damage to the structure by analyzing at least the sensor data; and/or (3) cause an indication of the detected water damage to be presented to a user. The instructions may direct additional, less, or alternate functionality, including that discussed elsewhere herein.

ADDITIONAL CONSIDERATIONS

The following considerations also apply to the foregoing discussion. Throughout this specification, plural instances may implement operations or structures described as a single instance. Although individual operations of one or more methods are illustrated and described as separate operations, one or more of the individual operations may be performed concurrently, and nothing requires that the operations be performed in the order illustrated. These and other variations, modifications, additions, and improvements fall within the scope of the subject matter herein.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one" aspect or "an" aspect means that a particular element, feature, structure, or characteristic described in connection with the aspect is included in at least one aspect. The appearances of the phrase "in one aspect" in various places in the specification are not necessarily all referring to the same aspect.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present). As used herein, the term "set" may include a collection of one or more elements.

In addition, use of "a" or "an" is employed to describe elements and components of the aspects herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for implementing the concepts disclosed herein, through the principles disclosed herein. Thus, while particular aspects and applications have been illustrated and described, it is to be understood that the disclosed aspects are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

We claim:

1. A system for detecting water damage to a structure, the system comprising:
   a plurality of energy-harvesting sensors on or within the structure, wherein each sensor of the plurality of energy-harvesting sensors is configured to (i) generate sensor data indicative of one or more characteristics of air, construction materials, and/or water within the structure and (ii) generate power for operating the sensor responsively to an external stimulus other than an electrical power source;
   one or more processors; and
   one or more memories storing instructions that, when executed by the one or more processors, cause the one or more processors to perform a method comprising:
      receiving sensor data generated by the plurality of energy-harvesting sensors,
      detecting water damage to the structure by analyzing at least the sensor data, and
      causing an indication of the detected water damage to be presented to a user.

2. The system of claim 1, wherein the plurality of energy-harvesting sensors includes one or more sensors each configured to generate power for operating the sensor responsively to water flowing past the sensor.

3. The system of claim 2, wherein the one or more sensors are positioned within one or more pipes or fixtures of the structure.

4. The system of claim 1, wherein the plurality of energy-harvesting sensors includes one or more sensors each (i) comprising a material configured to expand when becoming wet and (ii) configured to generate power for operating the sensor responsively to the material expanding.

5. The system of claim 1, wherein the plurality of energy-harvesting sensors includes one or more sensors each (i) comprising one or more solar cells and (ii) configured to generate power for operating the sensor responsively to the one or more solar cells collecting solar energy.

6. The system of claim 1, wherein the plurality of energy-harvesting sensors includes one or more sensors each of which is configured to generate power for operating the sensor responsively to a temperature differential across two regions of the sensor.

7. The system of claim 6, wherein the one or more sensors are positioned proximate to a water heater within the structure.

8. The system of claim 1, wherein the plurality of energy-harvesting sensors includes one or more energy-harvesting sensors embedded within construction materials of the structure.

9. The system of claim 1, wherein the sensor data is indicative of at least one characteristic of air within the structure, the at least one characteristic of air including one or more of:
   air temperature;
   air humidity;
   air movement; or
   airborne particle count.

10. The system of claim 1, wherein the sensor data is indicative of at least one characteristic of construction materials within the structure, the at least one characteristic of construction materials including or more of:
   moisture of the construction materials; or
   impedance of the construction materials.

11. The system of claim 1, wherein the sensor data is indicative of at least one characteristic of water within the structure, the at least one characteristic of water including or more of:
- a presence of pooled water within the structure; or
- a flow of water within the structure.

12. The system of claim 1, wherein causing the indication of the detected water damage to be presented to the user includes:
- generating an alert; and
- transmitting the alert to a device of the user.

13. The system of claim 12, wherein transmitting the alert includes:
- causing an application executing on a mobile device of the user to display the alert.

14. The system of claim 12, wherein the alert includes a report indicating one or more characteristics of the detected water damage, including at least a location of the detected water damage within the structure.

15. A computer-implemented method for detecting water damage to a structure, the computer-implemented method comprising:
- receiving sensor data generated by a plurality of energy-harvesting sensors on or within the structure, wherein each sensor of the plurality of energy-harvesting sensors is configured to (i) generate sensor data indicative of one or more characteristics of air, construction materials, and/or water within the structure and (ii) generate power for operating the sensor responsively to an external stimulus other than an electrical power source;
- detecting, by one or more processors, water damage to the structure by analyzing at least the sensor data; and
- causing, by the one or more processors, an indication of the detected water damage to be presented to a user.

16. The computer-implemented method of claim 15, wherein the plurality of energy-harvesting sensors includes one or more sensors each configured to generate power for operating the sensor responsively to water flowing past the sensor.

17. The computer-implemented method of claim 15, wherein the plurality of energy-harvesting sensors includes one or more sensors each (i) comprising a material configured to expand when becoming wet and (ii) configured to generate power for operating the sensor responsively to the material expanding.

18. The computer-implemented method of claim 15, wherein the plurality of energy-harvesting sensors includes one or more sensors each (i) comprising one or more solar cells and (ii) configured to generate power for operating the sensor responsively to the one or more solar cells collecting solar energy.

19. The computer-implemented method of claim 15, wherein the plurality of energy-harvesting sensors includes one or more sensors each of which is configured to generate power for operating the sensor responsively to a temperature differential across two regions of the sensor.

20. One or more tangible, non-transitory, computer-readable media storing instructions that, when executed by one or more processors, cause the one or more processors to:
- receive sensor data generated by a plurality of energy-harvesting sensors on or within the structure, wherein each sensor of the plurality of energy-harvesting sensors is configured to (i) generate sensor data indicative of one or more characteristics of air, construction materials, and/or water within the structure and (ii) generate power for operating the sensor responsively to an external stimulus other than an electrical power source;
- detect water damage to the structure by analyzing at least the sensor data; and
- cause an indication of the detected water damage to be presented to a user.

* * * * *